(12) United States Patent
Bauer et al.

(10) Patent No.: US 7,098,336 B2
(45) Date of Patent: Aug. 29, 2006

(54) FXR NR1H4 NUCLEAR RECEPTOR BINDING COMPOUNDS

(75) Inventors: Ulrike Bauer, Sandhausen (DE); Zach Cheruvallath, San Diego, CA (US); Ulrich Deuschle, Bammental (DE); Elena Dneprovskaia, San Diego, CA (US); Tim Gahman, Encinitas, CA (US); Kristina Giegrich, Lampertheim (DE); Ronnie Hanecak, San Clemente, CA (US); Normand Hébert, Cardiff, CA (US); John Kiely, San Diego, CA (US); Ingo Kober, Gaiberg (DE); Manfred Kögl, Eppelheim (DE); Harald Kranz, Leimen (DE); Claus Kremoser, Heidelberg (DE); Matthew Lee, Solana Beach, CA (US); Kerstin Otte, Heidelberg (DE); Carlton Sage, Cardiff, CA (US); Manish Sud, San Diego, CA (US)

(73) Assignee: Phenex Pharmaceuticals AG, Ludwigshafen (DE)

( * ) Notice: Subject to any disclaimer, the term of this patent is extended or adjusted under 35 U.S.C. 154(b) by 0 days.

(21) Appl. No.: 10/217,141

(22) Filed: Aug. 13, 2002

(65) Prior Publication Data
US 2003/0130296 A1 Jul. 10, 2003

(30) Foreign Application Priority Data
Aug. 13, 2001 (EP) .................................. 01119473

(51) Int. Cl.
*C07D 239/42* (2006.01)
*A61K 31/505* (2006.01)
*A61K 31/506* (2006.01)
*A61P 35/00* (2006.01)
(52) U.S. Cl. ........................ 544/331; 544/332; 514/275
(58) Field of Classification Search ................ 544/330, 544/332, 331; 514/275
See application file for complete search history.

(56) References Cited

U.S. PATENT DOCUMENTS 5,786,355 A * 7/1998 Konno et al. ................ 544/297
6,051,574 A 4/2000 Anthony
6,531,479 B1 * 3/2003 Wang et al. ................. 514/275

FOREIGN PATENT DOCUMENTS

DE 4237768 A1 * 5/1993

OTHER PUBLICATIONS

Bennett, Cecil Textbook of Medicine, 20th edition, vol. 1, 1004-1010, 1997.*
Wilson et al. Med. Res. Rev. 21(6): 513-522, 2001.*
Kast et al., Mol. Endocrinol., 15(10): 1720-1726, 2001.*
Patil et al., Indian Journal of Heterocyclic Chemistry, 11(2): 132-134, 2001.*
Bhat et al., Pharmacy and Pharmacology Communications, 6(12): 553-557, 2000.*
Naik et al., Asian Journal of Chemistry, 12(4): 1373-1374, 2000.*
Sharma et al., Indian Journal of Chemistry, 38B(8): 966-968, 1999.*
Murthy et al., Indian Journal of Heterocyclic Chemistry, 8(4): 277-280, 1999.*
Mehta et al., Asian Journal of Heterocyclic Chemistry, 10(4): 1017-1018, 1998.*
Kadu et al., Research Journal of Chemistry and Environment, 2(1): 69-71, 1998.*
Hussain et al., Asian Journal of Heterocyclic Chemistry, 9(1): 86-90, 1997.*
Modi et al., Asian Journal of Heterocyclic Chemistry, 6(4): 1061-1062, 1997.*
Modi et al., Asian Journal of Heterocyclic Chemistry, 6(4): 945-949, 1997.*
Abdel-Halim et al., Indian Journal of Heterocyclic Chemistry, 3(3): 165-170, 1994.*
Wendelin et al., Monatshefte fuer Chemie 115(3): 309-325, 1984.*
Ankhiwala et al., Journal of Institution of Chemists (India), 62(3): 115-116, 1990.*
Ankhiwala et al., Journal of Indian Chemical Society, 66(6): 417-418, 1989.*
Thakar et al., Journal of Indian Chemical Society, 60(7): 671-673, 1983.*
West, Anthony R., Solid State Chemistry and its Applications, Wiley, New York, 1988, pp. 358 & 365.*
Vippagunta et al., Advanced Drug Delivery Reviews 48: 3-26, 2001.*
"2-Amino-4,6-diarypyridines as Novel Ligands for the Estrogen Receptor." Brad r. Henke et al., *Bioorganic & Medical Chemistry Letters 11* (2001), pp. 1939-1942.
"Syntheses of 2-Alkylamino- and 2-Dialkylamino-4,6-diarylpyridines and 2,4,6-Trisustituted Pyrimidines Using Solid-Phase-Bound Chalcones." Alan R. Katritzky et al., *J. Comb. Chem.* (2000), vol. 2, pp. 182-185.

* cited by examiner

Primary Examiner—Venkataraman Balasubramanian
(74) Attorney, Agent, or Firm—Saliwanchik, Lloyd & Saliwanchik

(57) ABSTRACT

The invention provides compounds according to the general formula (1) which bind to the NR1H4 receptor and act as agonists, antagonists or mixed agonists/antagonists of the NR1H4 receptor. The invention further provides methods of treating diseases and/or conditions through binding of the nuclear receptor by the compounds and the production of medicaments using the compounds.

13 Claims, 9 Drawing Sheets

Fig. 2A

```
MGSKMNLIEH SHLPTTDEFS FSENLFGVLT EQVAGPLGQN LEVEPYSQYS NVQFPQVQPQ    60
ISSSSYYSNL GFYPQQPEEW YSPGIYELRR MPAETLYQGE TEVAEMPVTK KPRMGASAGR   120
IKGDELCVVC GDRASGYHYN ALTCEGCKGF FRRSITKNAV YKCKNGGNCV MDMYMRRKCQ   180
ECRLRKCKEM GMLAECMYTG LLTEIQCKSK RLRKNVKQHA DQTVNEDSEG RDLRQVTSTT   240
KSCREKTELT PDQQTLLHFI MDSYNKQRMP QEITNKILKE EFSAEENFLI LTEMATNHVQ   300
VLVEFTKKLP GFQTLDHEDQ IALLKGSAVE AMFLRSAEIF NKKLPSGHSD LLEERIRNSG   360
ISDEYITPMF SFYKSIGELK MTQEEYALLT AIVILSPDRQ YIKDREAVEK LQEPLLDVLQ   420
KLCKIHQPEN PQHFACLLGR LTELRTFNHH HAEMLMSWRV NDHKFTPLLC EIWDVQ       476
```

Fig. 2B

```
atgggatcaa aaatgaatct cattgaacat tcccatttac ctaccacaga tgaattttct      60
ttttctgaaa atttatttgg tgttttaaca gaacaagtgg caggtcctct gggacagaac    120
ctggaagtgg aaccatactc gcaatacagc aatgttcagt ttccccaagt tcaaccacag    180
atttcctcgt catcctatta ttccaacctg ggtttctacc cccagcagcc tgaagagtgg    240
tactctcctg gaatatatga actcaggcgt atgccagctg agactctcta ccaggagaa     300
actgaggtag cagagatgcc tgtaacaaag aagccccgca tgggcgcgtc agcagggagg    360
atcaaagggg atgagctgtg tgttgtttgt ggagacagag cctctggata ccactataat    420
gcactgacct gtgaggggtg taaaggtttc ttcaggagaa gcattaccaa aaacgctgtg    480
tacaagtgta aaaacggggg caactgtgtg atggatatgt acatgcgaag aaagtgtcaa    540
gagtgtcgac taaggaaatg caaagagatg ggaatgttgg ctgaatgtat gtatacaggc    600
ttgttaactg aaattcagtg taaatctaag cgactgagaa aaatgtgaa gcagcatgca     660
gatcagaccg tgaatgaaga cagtgaaggt cgtgacttgc gacaagtgac ctcgacaaca    720
aagtcatgca gggagaaaac tgaactcacc ccagatcaac agactcttct acattttatt    780
atggattcat ataacaaaca gaggatgcct caggaaataa caaataaaat tttaaaagaa    840
gaattcagtg cagaagaaaa ttttctcatt ttgacggaaa tggcaaccaa tcatgtacag    900
gttcttgtag aattcacaaa aagctacca ggatttcaga ctttggacca tgaagaccag     960
attgctttgc tgaaagggtc tgcggttgaa gctatgttcc ttcgttcagc tgagattttc   1020
aataagaaac ttccgtctgg gcattctgac ctattggaag aaagaattcg aaatagtggt   1080
atctctgatg aatatataac acctatgttt agttttata aagtattgg ggaactgaaa     1140
atgactcaag aggagtatgc tctgcttaca gcaattgtta cctgtctcc agatagacaa    1200
tacataaagg atagagaggc agtagagaag cttcaggagc cacttcttga tgtgctacaa   1260
aagttgtgta agattcacca gcctgaaaat cctcaacact ttgcctgtct cctgggtcgc   1320
ctgactgaat tacggacatt caatcatcac cacgctgaga tgctgatgtc atggagagta   1380
aacgaccaca agtttacccc acttctctgt gaaatctggg acgtgcagtg a            1431
```

Fig. 2C

```
MLVKPLPDSE EEGHDNQEAH QKYETMQCFA VSQPKSIKEE GEDLQSCLIC VARRVPMKER      60
PVLPSSESFT TRQDLQGKIT SLDTSTMRAA MKPGWEDLVR RCIQKFHAQH EGESVSYAKR     120
HHHEVLRQGL AFSQIYRFSL SDGTLVAAQT KSKLIRSQTT NEPQLVISLH MLHREQNVCV     180
MNPDLTGQTM GKPLNPISSN SPAHQALCSG NPGQDMTLSS NINFPINGPK EQMGMPMGRF     240
GGSGGMNHVS GMQATTPQGS NYALKMNSPS QSSPGMNPGQ PTSMLSPRHR MSPGVAGSPR     300
IPPSQFSPAG SLHSPVGVCS STGNSHSYTN SSLNALQALS EGHGVSLGSS LASPDLKMGN     360
LQNSPVNMNP PPLSKMGSLD SKDCFGLYGE PSEGTTGQAE SSCHPGEQKE TNDPNLPPAV     420
SSERADGQSR LHDSKGQTKL LQLLTTKSDQ MEPSPLASSL SDTNKDSTGS LPGSGSTHGT     480
SLKEKHKILH RLLQDSSSPV DLAKLTAEAT GKDLSQESSS TAPGSEVTIK QEPVSPKKKE     540
NALLRYLLDK DDTKDIGLPE ITPKLERLDS KTDPASNTKL IAMKTEKEEM SFEPGDQPGS     600
ELDNLEEILD DLQNSQLPQL FPDTRPGAPA GSVDKQAIIN DLMQLTAENS PVTPVGAQKT     660
ALRISQSTFN NPRPGQLGRL LPNQNLPLDI TLQSPTGAGP FPPIRNSSPY SVIPQPGMMG     720
NQGMIGNQGN LGNSSTGMIG NSASRPTMPS GEWAPQSSAV RVTCAATTSA MNRPVQGGMI     780
RNPAASIPMR PSSQPGQRQT LQSQVMNIGP SELEMNMGGP QYSQQQAPPN QTAPWPESIL     840
PIDQASFASQ NRQPFGSSPD DLLCPHPAAE SPSDEGALLD QLYLALRNFD GLEEIDRALG     900
IPELVSQSQA VDPEQFSSQD SNIMLEQKAP VFPQQYASQA QMAQGSYSPM QDPNFHTMGQ     960
RPSYATLRMQ PRPGLRPTGL VQNQPNQLRL QLQHRLQAQQ NRQPLMNQIS NVSNVNLTLR    1020
PGVPTQAPIN AQMLAQRQRE ILNQHLRQRQ MHQQQQVQQR TLMMRGQGLN MTPSMVAPSG    1080
MPATMSNPRI PQANAQQFPF PPNYGISQQP DPGFTGATTP QSPLMSPRMA HTQSPMMQQS    1140
QANPAYQAPS DINGWAQGNM GGNSMFSQQS PPHFGQQANT SMYSNNMNIN VSMATNTGGM    1200
SSMNQMTGQI SMTSVTSVPT SGLSSMGPEQ VNDPALRGGN LFPNQLPGMD MIKQEGDTTR    1260
KYC                                                                 1263
```

Fig. 2D

```
   1 ggcggccgca gcctcggcta cagcttcggc ggcgaaggtc agcgccgacg gcagccggca
  61 cctgacggcg tgaccgaccc gagccgattt ctcttggatt tggctacaca cttatagatc
 121 ttctgcactg tttacaggca cagttgctga tatgtgttca agatgagtgg gatgggagaa
 181 aatacctctg accccctccag ggcagagaca agaaagcgca aggaatgtcc tgaccaactt
 241 ggacccagcc ccaaaaggaa cactgaaaaa cgtaatcgtg aacaggaaaa taaatatata
 301 gaagaacttg cagagttgat ttttgcaaat tttaatgata tagacaactt taacttcaaa
 361 cctgacaaat gtgcaatctt aaaagaaact gtgaagcaaa ttcgtcagat caaagaacaa
 421 gagaaagcag cagctgccaa catagatgaa gtgcagaagt cagatgtatc ctctacaggg
 481 cagggtgtca tcgacaagga tgcgctgggc cctatgatgc ttgaggccct tgatgggttc
 541 ttctttgtag tgaacctgga aggcaacgtt gtgtttgtgt cagagaatgt gacacagtat
 601 ctaaggtata accaagaaga gctgatgaac aaaagtgtat atagcatctt gcatgttggg
 661 gaccacacgg aatttgtcaa aaacctgctg ccaaagtcta taggtaaatg ggggatcttg
 721 gtctggcgaa cctccgaggc ggaacagcca taccttcaat tgtcggatgc tggtaaaacc
 781 tttacctgat tcagaagagg agggtcatga taaccaggaa gctcatcaga aatatgaaac
 841 tatgcagtgc ttcgctgtct ctcaaccaaa gtccatcaaa gaagaaggag aagatttgca
 901 gtcctgcttg atttgcgtgg caagaagagt tccatgaag gaaagaccag ttcttccctc
 961 atcagaaagt tttactactc gccaggatct ccaaggcaag atcacgtctc tggataccag
1021 caccatgaga gcagccatga accaggctg ggaggacctg gtaagaaggt gtattcagaa
1081 gttccatgcg cagcatgaag gagaatctgt gtcctatgct aagaggcatc atcatgaagt
1141 actgagacaa ggattggcat tcagtcaaat ctatcgtttt tccttgtctg atggcactct
1201 tgttgctgca caaacgaaga gcaaactcat ccgttctcag actactaatg aacctcaact
1261 tgtaatatct ttacatatgc ttcacagaga gcagaatgtg tgtgtgatga atccggatct
1321 gactggacaa acgatgggga agccactgaa tccaattagc tctaacagcc ctgccatca
1381 ggccctgtgc agtgggaacc caggtcagga catgacccctc agtagcaata taaatttttcc
1441 cataaatggc ccaaaggaac aaatgggcat gcccatgggc aggtttggtg gttctggggg
1501 aatgaaccat gtgtcaggca tgcaagcaac cactcctcag ggtagtaact atgcactcaa
1561 aatgaacagc ccctcacaaa gcagccctgg catgaatcca ggacagccca cctccatgct
1621 ttcaccaagg catcgcatga gccctggagt ggctggcagc cctcgaatcc cacccagtca
1681 gtttttcccct gcaggaagct tgcattcccc tgtgggagtt tgcagcagca caggaaatag
1741 ccatagttat accaacagct ccctcaatgc acttcaggcc ctcagcgagg ggcacgggt
1801 ctcattaggg tcatcgttgg cttcaccaga cctaaaaatg ggcaatttgc aaaactcccc
1861 agttaatatg aatcctcccc cactcagcaa gatgggaagc ttggactcaa aagactgttt
1921 tggactatat ggggagccct ctgaaggtac aactggacaa gcagagagca gctgccatcc
1981 tggagagcaa aaggaaacaa atgacccccaa cctgccccccg gccgtgagca gtgagagagc
2041 tgacggcag agcagactgc atgacagcaa agggcagacc aaactcctgc agctgctgac
2101 caccaaatct gatcagatgg agccctcgcc cttagccagc tctttgtcgg atacaaacaa
2161 agactccaca ggtagcttgc ctggttctgg gtctacacat ggaaccctcgc tcaaggagaa
2221 gcataaaatt ttgcacagac tcttgcagga cagcagttcc cctgtggact tggccaagtt
2281 aacagcagaa gccacaggca aagacctgag ccaggagtcc agcagcacag ctcctggatc
2341 agaagtgact attaaacaag agccggtgag ccccaagaag aagagaatg cactacttcg
2401 ctatttgcta gataaagatg atactaaaga tattggttta ccagaaataa cccccaaact
2461 tgagagactg gacagtaaga cagatcctgc cagtaacaca aaattaatag caatgaaaac
2521 tgagaaggag gagatgagct tgagcctgg tgaccagcct ggcagtgagc tggacaactt
2581 ggaggagatt ttggatgatt tgcagaatag tcaattacca cagcttttcc cagacacgag
```

Fig. 2 D (continued)

```
2641 gccaggcgcc cctgctggat cagttgacaa gcaagccatc atcaatgacc tcatgcaact
2701 cacagctgaa aacagccctg tcacacctgt tggagcccag aaaacagcac tgcgaatttc
2761 acagagcact tttaataacc cacgaccagg gcaactgggc aggttattgc caaaccagaa
2821 tttaccactt gacatcacat tgcaaagccc aactggtgct ggacctttcc caccaatcag
2881 aaacagtagt ccctactcag tgatacctca gccaggaatg atgggtaatc aagggatgat
2941 aggaaaccaa ggaaatttag gaacagtag cacaggaatg attggtaaca gtgcttctcg
3001 gcctactatg ccatctggag aatgggcacc gcagagttcg gctgtgagag tcacctgtgc
3061 tgctaccacc agtgccatga accggccagt ccaaggaggt atgattcgga acccagcagc
3121 cagcatcccc atgaggccca gcagccagcc tggccaaaga cagacgcttc agtctcaggt
3181 catgaatata gggccatctg aattagagat gaacatgggg ggacctcagt atagccaaca
3241 acaagctcct ccaaatcaga ctgccccatg gcctgaaagc atcctgccta tagaccaggc
3301 gtctttgcc agccaaaaca ggcagccatt tggcagttct ccagatgact tgctatgtcc
3361 acatcctgca gctgagtctc cgagtgatga gggagctctc ctggaccagc tgtatctggc
3421 cttgcggaat tttgatggcc tggaggagat tgatagagcc ttaggaatac ccgaactggt
3481 cagccagagc caagcagtag atccagaaca gttctcaagt caggattcca acatcatgct
3541 ggagcagaag gcgcccgttt cccacagca gtatgcatct caggcacaaa tggcccaggg
3601 tagctattct cccatgcaag atccaaactt tcacaccatg ggacagcggc ctagttatgc
3661 cacactccgt atgcagccca gaccgggcct caggcccacg ggcctagtgc agaaccagcc
3721 aaatcaacta agacttcaac ttcagcatcg cctccaagca cagcagaatc gccagccact
3781 tatgaatcaa atcagcaatg tttccaatgt gaacttgact ctgaggcctg gagtaccaac
3841 acaggcacct attaatgcac agatgctggc ccagagacag agggaaatcc tgaaccagca
3901 tcttcgacag agacaaatgc atcagcaaca gcaagttcag caacgaactt tgatgatgag
3961 aggacaaggg ttgaatatga caccaagcat ggtggctcct agtggtatgc agcaactat
4021 gagcaaccct cggattcccc aggcaaatgc acagcagttt ccatttcctc caaactacgg
4081 aataagtcag caacctgatc caggctttac tggggctacg actccccaga gcccacttat
4141 gtcaccccga atggcacata cacagagtcc catgatgcaa cagtctcagg ccaacccagc
4201 ctatcaggcc ccctccgaca taaatggatg ggcgcagggg aacatgggcg aaacagcat
4261 gttttcccag cagtccccac cacactttgg gcagcaagca acaccagca tgtacagtaa
4321 caacatgaac atcaatgtgt ccatggcgac caacacaggt ggcatgagca gcatgaacca
4381 gatgacagga cagatcagca tgacctcagt gacctccgtg cctacgtcag ggctgtcctc
4441 catgggtccc gagcaggtta atgatcctgc tctgaggga ggcaacctgt tcccaaacca
4501 gctgcctgga atggatatga ttaagcagga gggagacaca acacggaaat attgctgaca
4561 ctgctgaagc cagttgcttc ttcagctgac cgggctcact tgctcaaaac acttccagtc
4621 tggagagctg tgtctatttg tttcaaccca actgacctgc cagccggttc tgctagagca
4681 gacaggcctg gcctggttc ccagggtggc gtccactcgg ctgtggcagg aggagctgcc
4741 tcttctcttg acagtctgaa gctcgcatcc agacagtcgc tcagtctgtt cactgcattc
4801 accttagtgc aacttagatc tctcctgcaa aagtaaatgt tgacaggcaa atttcatacc
4861 catgtcagat tgaatgtatt taaatgtatg tatttaagga gaaccatgct cttgttctgt
4921 tcctgttcgg ttccagacac tggtttcttg ctttgtttc cctggctaac agtctagtgc
4981 aaaagattaa gattttatct gggggaaaga aaagaatttt ttaaaaaatt aaactaaaga
5041 tgttttaagc taaagcctga atttgggatg gaagcaggac agacaccgtg gacagcgctg
```

Fig. 2 D (continued)

```
5101 tatttacaga cacacccagt gcgtgaagac caacaaagtc acagtcgtat ctctagaaag
5161 ctctaaagac catgttggaa agagtctcca gttactgaac agatgaaaag gagcctgtga
5221 gagggctgtt aacattagca aatatttttt ccttgttttt tctttgttaa aaccaaactg
5281 gttcacctga atcatgaatt gagaagaaat aatttcatt tctaaattaa gtccctttta
5341 gtttgatcag acagcttgaa tcagcatctc ttcttccctg tcagcctgac tcttcccttc
5401 ccctctctca ttccccatac tccctatttt cattccttt ttaaaaaata atataagcta
5461 cagaaaccag gtaagccctt tatttcctta aatgttttgc cagccactta ccaattgcta
5521 agtattgaat ttcagaaaaa aaaaatgcat ttactggcaa ggagaagagc aaagttaagg
5581 cttgatacca atcgagctaa ggatacctgc tttggaagca tgtttattct gttccccagc
5641 aactctggcc tccaaaatgg gagaaaacgc cagtgtgttt aaattgatag cagatatcac
5701 gacagattta acctctgcca tgtgtttttt attttgtttt ttagcagtgc tgactaagcc
5761 gaagttttgt aaggtacata aaatccaatt tatatgtaaa caagcaataa tttaagttga
5821 gaacttatgt gttttaattg tataattttt gtgaggtata catattgtgg aattgactca
5881 aaaatgaggt acttcagtat taaattagat atcttcatag caatgtctcc taaaggtgtt
5941 ttgtaaagga tatcaatgcc ttgattagac ctaatttgta gacttaagac ttttttatttt
6001 ctaaaccttg tgattctgct tataagtcat ttatctaatc tatatgatat gcagccgctg
6061 taggaaccaa ttcttgattt ttatatgttt atattctttc ttaatgaacc ttagaaagac
6121 tacatgttac taagcaggcc acttttatgg ttgttttt
```

| | BOTTOM | TOP | LOGEC50 | EC50 |
|---|---|---|---|---|
| CDCA | 6.468 | 43.26 | 0.9114 | 8.155 |
| 12996_3 | 8.794 | 35.75 | -0.5917 | 0.2560 |
| GW | 5.473 | 47.31 | -0.2576 | 0.5526 |
| LN0000006691 | 9.422 | 52.30 | -0.4886 | 0.3246 |

SEQUENCE LISTING

```
<160> NUMBER OF SEQ ID NOS: 5

<210> SEQ ID NO 1
<211> LENGTH: 476
<212> TYPE: PRT
<213> ORGANISM: Homo sapiens

<400> SEQUENCE: 1

Met Gly Ser Lys Met Asn Leu Ile Glu His Ser His Leu Pro Thr Thr
 1               5                  10                  15

Asp Glu Phe Ser Phe Ser Glu Asn Leu Phe Gly Val Leu Thr Glu Gln
            20                  25                  30

Val Ala Gly Pro Leu Gly Gln Asn Leu Glu Val Glu Pro Tyr Ser Gln
        35                  40                  45

Tyr Ser Asn Val Gln Phe Pro Gln Val Gln Pro Gln Ile Ser Ser Ser
    50                  55                  60

Ser Tyr Tyr Ser Asn Leu Gly Phe Tyr Pro Gln Gln Pro Glu Glu Trp
65                  70                  75                  80

Tyr Ser Pro Gly Ile Tyr Glu Leu Arg Arg Met Pro Ala Glu Thr Leu
                85                  90                  95

Tyr Gln Gly Glu Thr Glu Val Ala Glu Met Pro Val Thr Lys Lys Pro
            100                 105                 110

Arg Met Gly Ala Ser Ala Gly Arg Ile Lys Gly Asp Glu Leu Cys Val
        115                 120                 125

Val Cys Gly Asp Arg Ala Ser Gly Tyr His Tyr Asn Ala Leu Thr Cys
    130                 135                 140
```

```
Glu Gly Cys Lys Gly Phe Phe Arg Arg Ser Ile Thr Lys Asn Ala Val
145                 150                 155                 160

Tyr Lys Cys Lys Asn Gly Gly Asn Cys Val Met Asp Met Tyr Met Arg
                165                 170                 175

Arg Lys Cys Gln Glu Cys Arg Leu Arg Lys Cys Lys Glu Met Gly Met
            180                 185                 190

Leu Ala Glu Cys Met Tyr Thr Gly Leu Leu Thr Glu Ile Gln Cys Lys
        195                 200                 205

Ser Lys Arg Leu Arg Lys Asn Val Lys Gln His Ala Asp Gln Thr Val
210                 215                 220

Asn Glu Asp Ser Glu Gly Arg Asp Leu Arg Gln Val Thr Ser Thr Thr
225                 230                 235                 240

Lys Ser Cys Arg Glu Lys Thr Glu Leu Thr Pro Asp Gln Gln Thr Leu
                245                 250                 255

Leu His Phe Ile Met Asp Ser Tyr Asn Lys Gln Arg Met Pro Gln Glu
            260                 265                 270

Ile Thr Asn Lys Ile Leu Lys Glu Glu Phe Ser Ala Glu Glu Asn Phe
        275                 280                 285

Leu Ile Leu Thr Glu Met Ala Thr Asn His Val Gln Val Leu Val Glu
290                 295                 300

Phe Thr Lys Lys Leu Pro Gly Phe Gln Thr Leu Asp His Glu Asp Gln
305                 310                 315                 320

Ile Ala Leu Leu Lys Gly Ser Ala Val Glu Ala Met Phe Leu Arg Ser
                325                 330                 335

Ala Glu Ile Phe Asn Lys Lys Leu Pro Ser Gly His Ser Asp Leu Leu
            340                 345                 350

Glu Glu Arg Ile Arg Asn Ser Gly Ile Ser Asp Glu Tyr Ile Thr Pro
        355                 360                 365

Met Phe Ser Phe Tyr Lys Ser Ile Gly Glu Leu Lys Met Thr Gln Glu
370                 375                 380

Glu Tyr Ala Leu Leu Thr Ala Ile Val Ile Leu Ser Pro Asp Arg Gln
385                 390                 395                 400

Tyr Ile Lys Asp Arg Glu Ala Val Glu Lys Leu Gln Glu Pro Leu Leu
                405                 410                 415

Asp Val Leu Gln Lys Leu Cys Lys Ile His Gln Pro Glu Asn Pro Gln
            420                 425                 430

His Phe Ala Cys Leu Leu Gly Arg Leu Thr Glu Leu Arg Thr Phe Asn
        435                 440                 445

His His His Ala Glu Met Leu Met Ser Trp Arg Val Asn Asp His Lys
450                 455                 460

Phe Thr Pro Leu Leu Cys Glu Ile Trp Asp Val Gln
465                 470                 475

<210> SEQ ID NO 2
<211> LENGTH: 1431
<212> TYPE: DNA
<213> ORGANISM: Homo sapiens

<400> SEQUENCE: 2
atgggatcaa aaatgaatct cattgaacat tcccatttac ctaccacaga tgaattttct      60
ttttctgaaa atttatttgg tgttttaaca gaacaagtgg caggtcctct gggacagaac     120
ctggaagtgg aaccatactc gcaatacagc aatgttcagt ttcccccaagt tcaaccacag    180 atttcctcgt catcctatta ttccaacctg ggtttctacc cccagcagcc tgaagagtgg     240
```

-continued

| | |
|---|---|
| tactctcctg gaatatatga actcaggcgt atgccagctg agactctcta ccagggagaa | 300 |
| actgaggtag cagagatgcc tgtaacaaag aagccccgca tgggcgcgtc agcagggagg | 360 |
| atcaaagggg atgagctgtg tgttgtttgt ggagacagag cctctggata ccactataat | 420 |
| gcactgacct gtgagggtg taaaggtttc ttcaggagaa gcattaccaa aaacgctgtg | 480 |
| tacaagtgta aaacggggg caactgtgtg atggatatgt acatgcgaag aaagtgtcaa | 540 |
| gagtgtcgac taaggaaatg caagagatg ggaatgttgg ctgaatgtat gtatacaggc | 600 |
| ttgttaactg aaattcagtg taaatctaag cgactgagaa aaatgtgaa gcagcatgca | 660 |
| gatcagaccg tgaatgaaga cagtgaaggt cgtgacttgc dacaagtgac ctcgacaaca | 720 |
| aagtcatgca gggagaaaac tgaactcacc ccagatcaac agactcttct acattttatt | 780 |
| atggattcat ataacaaaca gaggatgcct caggaaataa caaataaaat tttaaaagaa | 840 |
| gaattcagtg cagaagaaaa ttttctcatt ttgacggaaa tggcaaccaa tcatgtacag | 900 |
| gttcttgtag aattcacaaa aaagctacca ggatttcaga cttttggacca tgaagaccag | 960 |
| attgctttgc tgaaagggtc tgcggttgaa gctatgttcc ttcgttcagc tgagattttc | 1020 |
| aataagaaac ttccgtctgg gcattctgac ctattggaag aaagaattcg aaatagtggt | 1080 |
| atctctgatg aatatataac acctatgttt agttttttata aaagtattgg ggaactgaaa | 1140 |
| atgactcaag aggagtatgc tctgcttaca gcaattgtta cctgtctcc agatagacaa | 1200 |
| tacataaagg atagagaggc agtagagaag cttcaggagc cacttcttga tgtgctacaa | 1260 |
| aagttgtgta agattcacca gcctgaaaat cctcaacact ttgcctgtct cctgggtcgc | 1320 |
| ctgactgaat tacggacatt caatcatcac cacgctgaga tgctgatgtc atggagagta | 1380 |
| aacgaccaca gtttaccccc acttctctgt gaaatctggg acgtgcagtg a | 1431 |

<210> SEQ ID NO 3
<211> LENGTH: 1263
<212> TYPE: PRT
<213> ORGANISM: Homo sapiens

<400> SEQUENCE: 3

```
Met Leu Val Lys Pro Leu Pro Asp Ser Glu Glu Gly His Asp Asn
  1               5                  10                  15

Gln Glu Ala His Gln Lys Tyr Glu Thr Met Gln Cys Phe Ala Val Ser
                 20                  25                  30

Gln Pro Lys Ser Ile Lys Glu Gly Glu Asp Leu Gln Ser Cys Leu
             35                  40                  45

Ile Cys Val Ala Arg Arg Val Pro Met Lys Glu Arg Pro Val Leu Pro
         50                  55                  60

Ser Ser Glu Ser Phe Thr Thr Arg Gln Asp Leu Gln Gly Lys Ile Thr
 65                  70                  75                  80

Ser Leu Asp Thr Ser Thr Met Arg Ala Ala Met Lys Pro Gly Trp Glu
                     85                  90                  95

Asp Leu Val Arg Arg Cys Ile Gln Lys Phe His Ala Gln His Glu Gly
                100                 105                 110

Glu Ser Val Ser Tyr Ala Lys Arg His His Glu Val Leu Arg Gln
            115                 120                 125

Gly Leu Ala Phe Ser Gln Ile Tyr Arg Phe Ser Leu Ser Asp Gly Thr
        130                 135                 140

Leu Val Ala Ala Gln Thr Lys Ser Lys Leu Ile Arg Ser Gln Thr Thr
145                 150                 155                 160
```

-continued

```
Asn Glu Pro Gln Leu Val Ile Ser Leu His Met Leu His Arg Glu Gln
            165                 170                 175
Asn Val Cys Val Met Asn Pro Asp Leu Thr Gly Gln Thr Met Gly Lys
        180                 185                 190
Pro Leu Asn Pro Ile Ser Ser Asn Ser Pro Ala His Gln Ala Leu Cys
    195                 200                 205
Ser Gly Asn Pro Gly Gln Asp Met Thr Leu Ser Ser Asn Ile Asn Phe
210                 215                 220
Pro Ile Asn Gly Pro Lys Glu Gln Met Gly Met Pro Met Gly Arg Phe
225                 230                 235                 240
Gly Gly Ser Gly Gly Met Asn His Val Ser Gly Met Gln Ala Thr Thr
                245                 250                 255
Pro Gln Gly Ser Asn Tyr Ala Leu Lys Met Asn Ser Pro Ser Gln Ser
            260                 265                 270
Ser Pro Gly Met Asn Pro Gly Gln Pro Thr Ser Met Leu Ser Pro Arg
        275                 280                 285
His Arg Met Ser Pro Gly Val Ala Gly Ser Pro Arg Ile Pro Pro Ser
    290                 295                 300
Gln Phe Ser Pro Ala Gly Ser Leu His Ser Pro Val Gly Val Cys Ser
305                 310                 315                 320
Ser Thr Gly Asn Ser His Ser Tyr Thr Asn Ser Ser Leu Asn Ala Leu
                325                 330                 335
Gln Ala Leu Ser Glu Gly His Gly Val Ser Leu Gly Ser Ser Leu Ala
            340                 345                 350
Ser Pro Asp Leu Lys Met Gly Asn Leu Gln Asn Ser Pro Val Asn Met
        355                 360                 365
Asn Pro Pro Leu Ser Lys Met Gly Ser Leu Asp Ser Lys Asp Cys
    370                 375                 380
Phe Gly Leu Tyr Gly Glu Pro Ser Glu Gly Thr Thr Gly Gln Ala Glu
385                 390                 395                 400
Ser Ser Cys His Pro Gly Glu Gln Lys Glu Thr Asn Asp Pro Asn Leu
                405                 410                 415
Pro Pro Ala Val Ser Ser Glu Arg Ala Asp Gly Gln Ser Arg Leu His
            420                 425                 430
Asp Ser Lys Gly Gln Thr Lys Leu Leu Gln Leu Leu Thr Thr Lys Ser
        435                 440                 445
Asp Gln Met Glu Pro Ser Pro Leu Ala Ser Ser Leu Ser Asp Thr Asn
    450                 455                 460
Lys Asp Ser Thr Gly Ser Leu Pro Gly Ser Gly Ser Thr His Gly Thr
465                 470                 475                 480
Ser Leu Lys Glu Lys His Lys Ile Leu His Arg Leu Leu Gln Asp Ser
                485                 490                 495
Ser Ser Pro Val Asp Leu Ala Lys Leu Thr Ala Glu Ala Thr Gly Lys
            500                 505                 510
Asp Leu Ser Gln Glu Ser Ser Thr Ala Pro Gly Ser Glu Val Thr
        515                 520                 525
Ile Lys Gln Glu Pro Val Ser Pro Lys Lys Glu Asn Ala Leu Leu
    530                 535                 540
Arg Tyr Leu Leu Asp Lys Asp Asp Thr Lys Asp Ile Gly Leu Pro Glu
545                 550                 555                 560
Ile Thr Pro Lys Leu Glu Arg Leu Asp Ser Lys Thr Asp Pro Ala Ser
                565                 570                 575
```

```
-continued

Asn Thr Lys Leu Ile Ala Met Lys Thr Glu Lys Glu Met Ser Phe
            580                 585                 590

Glu Pro Gly Asp Gln Pro Gly Ser Glu Leu Asp Asn Leu Glu Glu Ile
        595                 600                 605

Leu Asp Asp Leu Gln Asn Ser Gln Leu Pro Gln Leu Phe Pro Asp Thr
    610                 615                 620

Arg Pro Gly Ala Pro Ala Gly Ser Val Asp Lys Gln Ala Ile Ile Asn
625                 630                 635                 640

Asp Leu Met Gln Leu Thr Ala Glu Asn Ser Pro Val Thr Pro Val Gly
                645                 650                 655

Ala Gln Lys Thr Ala Leu Arg Ile Ser Gln Ser Thr Phe Asn Asn Pro
            660                 665                 670

Arg Pro Gly Gln Leu Gly Arg Leu Leu Pro Asn Gln Asn Leu Pro Leu
        675                 680                 685

Asp Ile Thr Leu Gln Ser Pro Thr Gly Ala Gly Pro Phe Pro Pro Ile
    690                 695                 700

Arg Asn Ser Ser Pro Tyr Ser Val Ile Pro Gln Pro Gly Met Met Gly
705                 710                 715                 720

Asn Gln Gly Met Ile Gly Asn Gln Gly Asn Leu Gly Asn Ser Ser Thr
                725                 730                 735

Gly Met Ile Gly Asn Ser Ala Ser Arg Pro Thr Met Pro Ser Gly Glu
            740                 745                 750

Trp Ala Pro Gln Ser Ser Ala Val Arg Val Thr Cys Ala Ala Thr Thr
        755                 760                 765

Ser Ala Met Asn Arg Pro Val Gln Gly Gly Met Ile Arg Asn Pro Ala
    770                 775                 780

Ala Ser Ile Pro Met Arg Pro Ser Ser Gln Pro Gly Gln Arg Gln Thr
785                 790                 795                 800

Leu Gln Ser Gln Val Met Asn Ile Gly Pro Ser Glu Leu Glu Met Asn
                805                 810                 815

Met Gly Gly Pro Gln Tyr Ser Gln Gln Gln Ala Pro Pro Asn Gln Thr
            820                 825                 830

Ala Pro Trp Pro Glu Ser Ile Leu Pro Ile Asp Gln Ala Ser Phe Ala
        835                 840                 845

Ser Gln Asn Arg Gln Pro Phe Gly Ser Ser Pro Asp Asp Leu Leu Cys
    850                 855                 860

Pro His Pro Ala Ala Glu Ser Pro Ser Asp Glu Gly Ala Leu Leu Asp
865                 870                 875                 880

Gln Leu Tyr Leu Ala Leu Arg Asn Phe Asp Gly Leu Glu Glu Ile Asp
                885                 890                 895

Arg Ala Leu Gly Ile Pro Glu Leu Val Ser Gln Ser Gln Ala Val Asp
            900                 905                 910

Pro Glu Gln Phe Ser Ser Gln Asp Ser Asn Ile Met Leu Glu Gln Lys
        915                 920                 925

Ala Pro Val Phe Pro Gln Gln Tyr Ala Ser Gln Ala Gln Met Ala Gln
    930                 935                 940

Gly Ser Tyr Ser Pro Met Gln Asp Pro Asn Phe His Thr Met Gly Gln
945                 950                 955                 960

Arg Pro Ser Tyr Ala Thr Leu Arg Met Gln Pro Arg Pro Gly Leu Arg
                965                 970                 975

Pro Thr Gly Leu Val Gln Asn Gln Pro Asn Gln Leu Arg Leu Gln Leu
            980                 985                 990
```

```
Gln His Arg Leu Gln Ala Gln Gln Asn Arg Gln Pro Leu Met Asn Gln
        995                 1000                1005

Ile Ser Asn Val Ser Asn Val Asn Leu Thr Leu Arg Pro Gly Val Pro
   1010                1015                1020

Thr Gln Ala Pro Ile Asn Ala Gln Met Leu Ala Gln Arg Gln Arg Glu
1025                1030                1035                1040

Ile Leu Asn Gln His Leu Arg Gln Arg Gln Met His Gln Gln Gln
            1045                1050                1055

Val Gln Gln Arg Thr Leu Met Met Arg Gly Gln Gly Leu Asn Met Thr
        1060                1065                1070

Pro Ser Met Val Ala Pro Ser Gly Met Pro Ala Thr Met Ser Asn Pro
    1075                1080                1085

Arg Ile Pro Gln Ala Asn Ala Gln Gln Phe Pro Phe Pro Pro Asn Tyr
    1090                1095                1100

Gly Ile Ser Gln Gln Pro Asp Pro Gly Phe Thr Gly Ala Thr Thr Pro
1105                1110                1115                1120

Gln Ser Pro Leu Met Ser Pro Arg Met Ala His Thr Gln Ser Pro Met
            1125                1130                1135

Met Gln Gln Ser Gln Ala Asn Pro Ala Tyr Gln Ala Pro Ser Asp Ile
        1140                1145                1150

Asn Gly Trp Ala Gln Gly Asn Met Gly Gly Asn Ser Met Phe Ser Gln
        1155                1160                1165

Gln Ser Pro Pro His Phe Gly Gln Gln Ala Asn Thr Ser Met Tyr Ser
        1170                1175                1180

Asn Asn Met Asn Ile Asn Val Ser Met Ala Thr Asn Thr Gly Gly Met
1185                1190                1195                1200

Ser Ser Met Asn Gln Met Thr Gly Gln Ile Ser Met Thr Ser Val Thr
            1205                1210                1215

Ser Val Pro Thr Ser Gly Leu Ser Ser Met Gly Pro Glu Gln Val Asn
        1220                1225                1230

Asp Pro Ala Leu Arg Gly Gly Asn Leu Phe Pro Asn Gln Leu Pro Gly
        1235                1240                1245

Met Asp Met Ile Lys Gln Glu Gly Asp Thr Thr Arg Lys Tyr Cys
        1250                1255                1260

<210> SEQ ID NO 4
<211> LENGTH: 6158
<212> TYPE: DNA
<213> ORGANISM: Homo sapiens

<400> SEQUENCE: 4
ggcggccgca gcctcggcta cagcttcggc ggcgaaggtc agcgccgacg gcagccggca      60
cctgacggcg tgaccgaccc gagccgattt ctcttggatt tggctacaca cttatagatc     120
ttctgcactg tttacaggca cagttgctga tatgtgttca agatgagtgg gatgggagaa     180
aatacctctg accctccag ggcagagaca agaaagcgca aggaatgtcc tgaccaactt      240
ggacccagcc ccaaaaggaa cactgaaaaa cgtaatcgtg aacaggaaaa taaatatata     300
gaagaacttg cagagttgat ttttgcaaat tttaatgata tagacaactt taacttcaaa     360
cctgacaaat gtgcaatctt aaaagaaact gtgaagcaaa ttcgtcagat caaagaacaa     420
gagaaagcag cagctgccaa catagatgaa gtgcagaagt cagatgtatc ctctacaggg     480
cagggtgtca tcgacaagga tgcgctgggg cctatgatgc ttgaggccct tgatgggttc     540
ttctttgtag tgaacctgga aggcaacgtt gtgtttgtgt cagagaatgt gacacagtat     600
```

-continued

| | |
|---|---|
| ctaaggtata accaagaaga gctgatgaac aaaagtgtat atagcatctt gcatgttggg | 660 |
| gaccacacgg aatttgtcaa aaacctgctg ccaaagtcta taggtaaatg ggggatcttg | 720 |
| gtctggcgaa cctccgaggc ggaacagcca taccttcaat tgtcggatgc tggtaaaacc | 780 |
| tttacctgat tcagaagagg agggtcatga taaccaggaa gctcatcaga aatatgaaac | 840 |
| tatgcagtgc ttcgctgtct ctcaaccaaa gtccatcaaa gaagaaggag aagatttgca | 900 |
| gtcctgcttg atttgcgtgg caagaagagt tcccatgaag gaaagaccag ttcttccctc | 960 |
| atcagaaagt tttactactc gccaggatct ccaaggcaag atcacgtctc tggataccag | 1020 |
| caccatgaga gcagccatga aaccaggctg ggaggacctg taagaaggt gtattcagaa | 1080 |
| gttccatgcg cagcatgaag gagaatctgt gtcctatgct aagaggcatc atcatgaagt | 1140 |
| actgagacaa ggattggcat tcagtcaaat ctatcgtttt tccttgtctg atggcactct | 1200 |
| tgttgctgca caaacgaaga gcaaactcat ccgttctcag actactaatg aacctcaact | 1260 |
| tgtaatatct ttacatatgc ttcacagaga gcagaatgtg tgtgtgatga atccggatct | 1320 |
| gactggacaa acgatgggga agccactgaa tccaattagc tctaacagcc ctgcccatca | 1380 |
| ggccctgtgc agtgggaacc caggtcagga catgaccctc agtagcaata taaattttcc | 1440 |
| cataaatggc ccaaaggaac aaatgggcat gcccatgggc aggtttggtg ttctggggg | 1500 |
| aatgaaccat gtgtcaggca tgcaagcaac cactcctcag ggtagtaact atgcactcaa | 1560 |
| aatgaacagc ccctcacaaa gcagccctgg catgaatcca ggacagccca cctccatgct | 1620 |
| ttcaccaagg catcgcatga gccctggagt ggctggcagc cctcgaatcc cacccagtca | 1680 |
| gttttcccct gcaggaagct tgcattcccc tgtgggagtt tgcagcagca caggaaatag | 1740 |
| ccatagttat accaacagct ccctcaatgc acttcaggcc ctcagcgagg ggcacggggt | 1800 |
| ctcattaggg tcatcgttgg cttcaccaga cctaaaaatg ggcaatttgc aaaactcccc | 1860 |
| agttaatatg aatcctcccc cactcagcaa gatgggaagc ttggactcaa aagactgttt | 1920 |
| tggactatat ggggagccct ctgaaggtac aactggacaa gcagagagca gctgccatcc | 1980 |
| tggagagcaa aaggaaacaa atgacccca cctgccccg gccgtgagca gtgagagagc | 2040 |
| tgacgggcag agcagactgc atgacagcaa agggcagacc aaaactcctgc agctgctgac | 2100 |
| caccaaatct gatcagatgg agccctcgcc cttagccagc tctttgtcgg atacaaacaa | 2160 |
| agactccaca ggtagcttgc ctggttctgg gtctacacat ggaacctcgc tcaaggagaa | 2220 |
| gcataaaatt ttgcacagac tcttgcagga cagcagttcc cctgtggact tggccaagtt | 2280 |
| aacagcagaa gccacaggca aagacctgag ccaggagtcc agcagcacag ctcctggatc | 2340 |
| agaagtgact attaaacaag agccggtgag ccccaagaag aaagagaatg cactacttcg | 2400 |
| ctatttgcta gataaagatg atactaaaga tattggttta ccagaaataa cccccaaact | 2460 |
| tgagagactg gacagtaaga cagatcctgc cagtaacaca aaattaatag caatgaaaac | 2520 |
| tgagaaggag gagatgagct ttgagcctgg tgaccagcct ggcagtgagc tggacaactt | 2580 |
| ggaggagatt ttggatgatt tgcagaatag tcaattacca cagcttttcc cagacacgag | 2640 |
| gccaggcgcc cctgctggat cagttgacaa gcaagccatc atcaatgacc tcatgcaact | 2700 |
| cacagctgaa aacagccctg tcacacctgt tggagcccag aaaacagcac tgcgaatttc | 2760 |
| acagagcact tttaataacc cacgaccagg gcaactgggc aggttattgc caaaccagaa | 2820 |
| tttaccactt gacatcacat tgcaaagccc aactggtgct ggaccttttcc caccaatcag | 2880 |
| aaacagtagt ccctactcag tgataccttca gccaggaatg atgggtaatc aagggatgat | 2940 |
| aggaaaccaa ggaaatttag ggaacagtag cacaggaatg attggtaaca gtgcttctcg | 3000 |

```
gcctactatg ccatctggag aatgggcacc gcagagttcg gctgtgagag tcacctgtgc       3060
tgctaccacc agtgccatga accggccagt ccaaggaggt atgattcgga acccagcagc       3120
cagcatcccc atgaggccca gcagccagcc tggccaaaga cagacgcttc agtctcaggt       3180
catgaatata gggccatctg aattagagat gaacatgggg ggacctcagt atagccaaca       3240
acaagctcct ccaaatcaga ctgccccatg gcctgaaagc atcctgccta tagaccaggc       3300
gtcttttgcc agccaaaaca ggcagccatt tggcagttct ccagatgact tgctatgtcc       3360
acatcctgca gctgagtctc cgagtgatga gggagctctc ctggaccagc tgtatctggc       3420
cttgcggaat tttgatggcc tggaggagat tgatagagcc ttaggaatac ccgaactggt       3480
cagccagagc caagcagtag atccagaaca gttctcaagt caggattcca acatcatgct       3540
ggagcagaag gcgcccgttt cccacagca gtatgcatct caggcacaaa tggcccaggg       3600
tagctattct cccatgcaag atccaaactt tcacaccatg ggacagcggc ctagttatgc       3660
cacactccgt atgcagccca gaccgggcct caggcccacg ggcctagtgc agaaccagcc       3720
aaatcaacta agacttcaac ttcagcatcg cctccaagca cagcagaatc gccagccact       3780
tatgaatcaa atcagcaatg tttccaatgt gaacttgact ctgaggcctg gagtaccaac       3840
acaggcacct attaatgcac agatgctggc ccagagacag agggaaatcc tgaaccagca       3900
tcttcgacag agacaaatgc atcagcaaca gcaagttcag caacgaactt tgatgatgag       3960
aggacaaggg ttgaatatga caccaagcat ggtggctcct agtggtatgc cagcaactat       4020
gagcaaccct cggattcccc aggcaaatgc acagcagttt ccatttcctc caaactacgg       4080
aataagtcag caacctgatc caggctttac tggggctacg actccccaga gcccacttat       4140
gtcaccccga atggcacata cacagagtcc catgatgcaa cagtctcagg ccaacccagc       4200
ctatcaggcc ccctccgaca taaatggatg gcgcagggg aacatgggcg gaaacagcat       4260
gttttcccag cagtccccac cacactttgg gcagcaagca acaccagca tgtacagtaa       4320
caacatgaac atcaatgtgt ccatggcgac caacacaggt ggcatgagca gcatgaacca       4380
gatgacagga cagatcagca tgacctcagt gacctccgtg cctacgtcag ggctgtcctc       4440
catgggtccc gagcaggtta atgatcctgc tctgagggga ggcaacctgt tcccaaacca       4500
gctgcctgga atggatatga ttaagcagga gggagacaca acacggaaat attgctgaca       4560
ctgctgaagc cagttgcttc ttcagctgac cgggctcact tgctcaaaac acttccagtc       4620
tggagagctg tgtctatttg tttcaaccca actgacctgc cagccggttc tgctagagca       4680
gacaggcctg gccctggttc ccaggtggc gtccactcgg ctgtggcagg aggagctgcc       4740
tcttctcttg acagtctgaa gctcgcatcc agacagtcgc tcagtctgtt cactgcattc       4800
accttagtgc aacttagatc tctcctgcaa aagtaaatgt tgacaggcaa atttcatacc       4860
catgtcagat tgaatgtatt taaatgtatg tatttaagga gaaccatgct cttgttctgt       4920
tcctgttcgg ttccagacac tggtttcttg ctttgttttc cctggctaac agtctagtgc       4980
aaaagattaa gattttatct gggggaaaga aaagaatttt ttaaaaaatt aaactaaaga       5040
tgttttaagc taaagcctga atttgggatg gaagcaggac agacaccgtg gacagcgctg       5100
tatttacaga cacacccagt gcgtgaagac caacaaagtc acagtcgtat ctctagaaag       5160
ctctaaagac catgttggaa agagtctcca gttactgaac agatgaaaag gagcctgtga       5220
gagggctgtt aacattagca atatttttt ccttgttttt tctttgttaa aaccaaactg       5280
gttcacctga atcatgaatt gagaagaaat aattttcatt tctaaattaa gtccctttta       5340
gtttgatcag acagcttgaa tcagcatctc ttcttccctg tcagcctgac tcttcccttc       5400
```

```
                                                                  -continued ccctctctca ttccccatac tccctatttt cattccttttt ttaaaaaata atataagcta    5460
cagaaaccag gtaagccctt tatttcctta aatgttttgc cagccactta ccaattgcta    5520
agtattgaat ttcagaaaaa aaaaatgcat ttactggcaa ggagaagagc aaagttaagg    5580
cttgatacca atcgagctaa ggatacctgc tttggaagca tgtttattct gttccccagc    5640
aactctggcc tccaaaatgg gagaaaacgc cagtgtgttt aaattgatag cagatatcac    5700
gacagattta acctctgcca tgtgttttt attttgtttt ttagcagtgc tgactaagcc     5760
gaagttttgt aaggtacata aaatccaatt tatatgtaaa caagcaataa tttaagttga    5820
gaacttatgt gttttaattg tataattttt gtgaggtata catattgtgg aattgactca    5880
aaaatgaggt acttcagtat taaattagat atcttcatag caatgtctcc taaaggtgtt    5940
ttgtaaagga tatcaatgcc ttgattagac ctaatttgta gacttaagac tttttatttt    6000
ctaaaccttg tgattctgct tataagtcat ttatctaatc tatatgatat gcagccgctg    6060
taggaaccaa ttcttgattt ttatatgttt atattctttc ttaatgaacc ttagaaagac    6120
tacatgttac taagcaggcc acttttatgg ttgtttttt                           6158

<210> SEQ ID NO 5
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
cccagggtga ataacctcgg ggctctgtcc ctccaatccc agggtgaata acctcggg      58
```

FXR NR1H4 NUCLEAR RECEPTOR BINDING COMPOUNDS

FIELD OF THE INVENTION

The present invention relates to compounds according to the general formulae (1), (2), (3) and (4) which bind to the NR1H4 receptor and act as agonists, antagonists or mixed agonists/antagonists of the NR1H4 receptor. The invention further relates to the treatment of diseases and/or conditions through binding of said nuclear receptor by said compounds and the production of medicaments using said compounds.

BACKGROUND OF THE INVENTION

Multicellular organisms are dependent on advanced mechanisms of information transfer between cells and body compartments. The information that is transmitted can be highly complex and can result in the alteration of genetic programs involved in cellular differentiation, proliferation, or reproduction. The signals, or hormones, are often simple molecules, such as peptides, fatty acid, or cholesterol derivatives.

Many of these signals produce their effects by ultimately changing the transcription of specific genes. One well-studied group of proteins that mediate a cell's response to a variety of signals is the family of transcription factors known as nuclear receptors, hereinafter referred to often as "NR". Members of this group include receptors for steroid hormones, vitamin D, ecdysone, cis and trans retinoic acid, thyroid hormone, bile acids, cholesterol-derivatives, fatty acids (and other peroxisomal proliferators), as well as so-called orphan receptors, proteins that are structurally similar to other members of this group, but for which no ligands are known (Escriva, H. et al., Ligand binding was acquired during evolution of nuclear receptors, PNAS, 94, 6803–6808, 1997). Orphan receptors may be indicative of unknown signaling pathways in the cell or may be nuclear receptors that function without ligand activation. The activation of transcription by some of these orphan receptors may occur in the absence of an exogenous ligand and/or through signal transduction pathways originating from the cell surface (Mangelsdorf, D. J. et al., *The nuclear receptor superfamily: the second decade*, Cell 83, 835–839, 1995).

In general, three functional domains have been defined in NRs. An amino terminal domain is believed to have some regulatory function. A DNA-binding domain hereinafter referred to as "DBD" usually comprises two zinc finger elements and recognizes a specific Hormone Responsive Element hereinafter referred to as "HRE" within the promoters of responsive genes. Specific amino acid residues in the "DBD" have been shown to confer DNA sequence binding specificity (Schena, M. & Yamamoto, K. R., Mammalian Glucocorticoid Receptor Derivatives Enhance Transcription in Yeast, Science, 241:965–967, 1988). A Ligand-binding-domain hereinafter referred to as "LBD" is at the carboxy-terminal region of known NRs. In the absence of hormone, the LBD of some but not all NRs appears to interfere with the interaction of the DBD with its HRE. Hormone binding seems to result in a conformational change in the NR and thus opens this interference (Brzozowski et al., *Molecular basis of agonism and antagonism in the oestrogen receptor*, Nature, 389, 753–758, 1997; Wagner et al., *A structural role for hormone in the thyroid hormone receptor*, Nature, 378, 690–697, 1995). A NR without the HBD constitutively activates transcription but at a low level.

Coactivators or transcriptional activators are proposed to bridge between sequence specific transcription factors and the basal transcription machinery and in addition to influence the chromatin structure of a target cell. Several proteins like SRC-1, ACTR, and Grip1 interact with NRs in a ligand enhanced manner (Heery et al., *A signature motif in transcriptional coactivators mediates binding to nuclear receptors*, Nature, 387, 733–736; Heinzel et al., *A complex containing N-CoR, mSin3 and histone deacetylase mediates transcriptional repression*, Nature 387, 43–47, 1997). Furthermore, the physical interaction with repressing receptor-interacting proteins or corepressors has been demonstrated (Xu et al., Coactivator and *Corepressor complexes in nuclear receptor function*, Curr Opin Genet Dev, 9 (2), 140–147, 1999).

Nuclear receptor modulators like steroid hormones affect the growth and function of specific cells by binding to intracellular receptors and forming nuclear receptor-ligand complexes. Nuclear receptor-hormone complexes then interact with a hormone response element (HRE) in the control region of specific genes and alter specific gene expression.

The Farnesoid X Receptor alpha (FXR; hereinafter also often referred to as NR1H4 when referring to the human receptor) is a prototypical type 2 nuclear receptor which activates genes upon binding to promoter region of target genes in a heterodimeric fashion with Retinoid X Receptor (hereinafter RXR, Forman et al., Cell, 81, 687–93, 1995). The relevant physiological ligands of NR1H4 seem to be bile acids (Makishima et al., Science, 284, 1362–65, 1999; Parks et al., Science, 284, 1365–68,1999). The most potent is chenodeoxycholic acid, which regulates the expression of several genes that participate in bile acid homeostasis.

Farnesol, originally described to activate the rat ortholog at high concentration does not activate the human or mouse receptor. FXR is expressed in the liver, small intestine, colon, ovary, adrenal gland and kidney. Like LXR-α, NR1H4 is involved in autocrine signaling.

FXR is proposed to be a nuclear bile acid sensor. As a result, it modulates both, the synthetic output of bile acids from the liver and their recycling in the intestine (by regulating bile acid binding protein). Upon activation (e.g. binding of chenodeoxycholic acid), it influences the conversion of dietary cholesterol into bile acids by inhibiting the transcription of key genes which are involved in bile acid synthesis such as CYP7A1 or in bile acid transport across the hepatocyte membranes such as the bile acid transporters BSEP (Bile Salt Export Pump) and NTCP (Na-Taurocholate Co-Transporter). This seems to be a major mechanism of feedback regulation onto bile acid synthesis. Moreover, NR1H4 seems to be the crucial receptor for maintaining bile acid homeostasis within the hepatocyte and therefore might be an appropriate drug target to treat diseases that result from impaired bile acid production, impaired export into the bile canaliculi or impaired bile flow in general such as cholestatic conditions. Loss of function of NR1H4 results in major changes in bile acid homeostasis on the organism level (Lu, et al., Mol Cell. (2000) 6(3):507–15; Goodwin, et al., Mol Cell. (2000) 6(3):517–26; Sinal, et al., Cell (2000) 15; 102(6):731–44).

The synthetic compounds, 1,1-bisphosphonate esters, appear to display a number of similar activities to the two identified prototypes of natural FXR agonists, farnesol, and chenodeoxycholic acid. Like farnesol, the 1,1-bisphosphonate esters increase the rate of 3-hydroxy-3-methylglutaryl-CoA (HMG-CoA) reductase degradation and like bile acids they induce the expression of the Intestinal Bile Acid Binding Protein (I-BABP) and repress the cholesterol 7 α-hydroxylase gene. Certain 1,1-bisphosphonate esters also bind to FXR. (Niesor et al., Curr Pharm Des, 7(4):231–59, 2001). That means that activation of FXR could lead to opposing effects such as lowering the rate of cholesterol synthesis by increasing degradation of HMG-CoA Reductase and increasing the cholesterol pool by inhibition of cholesterol degradation into bile acids. The FXR agonist chenodeoxycholic acid does not change cholesterol and lipoprotein levels significantly in patients, although a repression of bile acid synthesis as well as a decreased HMG-CoA reductase activity was observed (Einarsson et al., Hepatology, 33(5), 1189–93, 2001) confirming that cellular cholesterol synthesis and degradation are controlled by numerous regulatory loops including the coordinate regulation of HMGCoA reductase and cholesterol 7α-hydroxylase and that compounds modulating FXR acitvity might have different effects on blood lipid parameters.

In the course of functional analysis of certain 1,1-bisphosphonate esters, it was shown that these compounds, which are known to bind to FXR also induce apoptosis in a variety of cell types, similar to the isporenoids farnesol and geranylgeraniol, which are also known as weak FXR binders (Flach et al., Biochem Biophys Res Com, 270, 240–46, 2000).

To date only very few compounds have been described which bind the NR1H4 receptor and thus show utility for treating diseases or conditions which are due to or influenced by said nuclear receptor (Maloney at al., J Med Chem, 10; 43(16):2971–4, 2000).

It is currently believed that FXR agonists might be useful to treat cholestatic conditions because they result in an upregulation of bile acid transport activity across the canalicular hepatocyte membrane (Plass, et al., Hepatology. (2002) 35(3):589–96; Willson, et al., Med Res Rev. (2001) 21(6):513–22). In contrast, it is believed that compounds that act as FXR antagonists or at least as mixed agonists/antagonists might reduce total serum cholesterol (Urizar, et al., Science (2002) 31; 296(5573):1703–6).

It is thus an object of the present invention to provide for novel NR1H4 binding compounds. It is thus an object of the present invention to provide for compounds which by means of binding the NR1H4 receptor act as agonist or antagonist or mixed agonist/antagonist of said receptor and thus show utility for treating diseases or conditions which are due to or influenced by said nuclear receptor.

It is further an object of the invention to provide for compounds which may be used for the manufacture of a medicament for the treatment of cholesterol or bile acid associated conditions or diseases. In a preferred embodiment of the invention, it is an object of the invention to provide for cholesterol lowering or anti-cholestatic compounds. It is also an object of the invention to provide for compounds that may be used for the manufacture of anticancer medicaments or apoptosis-inducing medicaments in general.

It is further an object of the invention to provide for compounds which are orally available and can be used for an oral treatment of the diseases mentioned afore.

SUMMARY OF THE INVENTION

The present invention provides, inter alia, novel NR1H4 nuclear receptor protein binding compounds according to the general formulae (1), (2), (3) and (4) shown below. Said compounds are also binders of mammalian homologues of said receptor. Further the object of the invention is solved by providing for amongst the NR1H4 nuclear receptor protein binding compounds according to the general formulae (1), (2), (3) and (4) such compounds which act as agonists and such compounds which act as antagonists or mixed agonists/antagonists of the human FXR receptor or a mammalian homologue thereof.

The invention provides for FXR agonists, which may be used for the manufacture of a medicament for the treatment of cholesterol associated conditions or diseases. In a preferred embodiment of the invention cholesterol lowering or cholestatic compounds are disclosed. The compounds according to the invention may be used for manufacture of antitumor medicaments and/or for the treatment or prevention of diseases such as cancer.

The invention provides for FXR agonists which may be used for the manufacture of a medicament for the treatment of cholesterol or bile acid associated conditions or diseases or for the treatment of hyperproliferative diseases such as cancer or for the treatment of drug resistance which results from continuous drug treatment of cancer or infectious diseases. In a preferred embodiment of the invention it is an object of the invention to provide for cholesterol lowering or anti-cholestatic compounds. It is also an object of the invention to provide for compounds that may be used for the manufacture of anticancer medicaments or apoptosis-inducing medicaments in general.

The foregoing merely summarizes certain aspects of the present invention and is not intended, nor should it be construed, to limit the invention in any manner. All patents and other publications recited herein are hereby incorporated by reference in their entirety.

BRIEF DESCRIPTION OF THE DRAWINGS

FIG. 2A shows SEQ ID NO. 1 which is the protein sequence of the FRX protein, a portion of which was used for cloning as described in the examples. FIG. 2B shows SEQ ID NO. 2 which is the mRNA sequence of the FXR protein. FIG. 2C shows SEQ ID NO. 3 which is the protein sequence of TIF2 (Acc. No: XM_011633 RefSeq DB), FIG. 2D shows SEQ ID NO. 4 which is the respective mRNA sequence corresponding to the TIF2 protein.

DETAILED DESCRIPTION OF THE INVENTION

Figure 1:
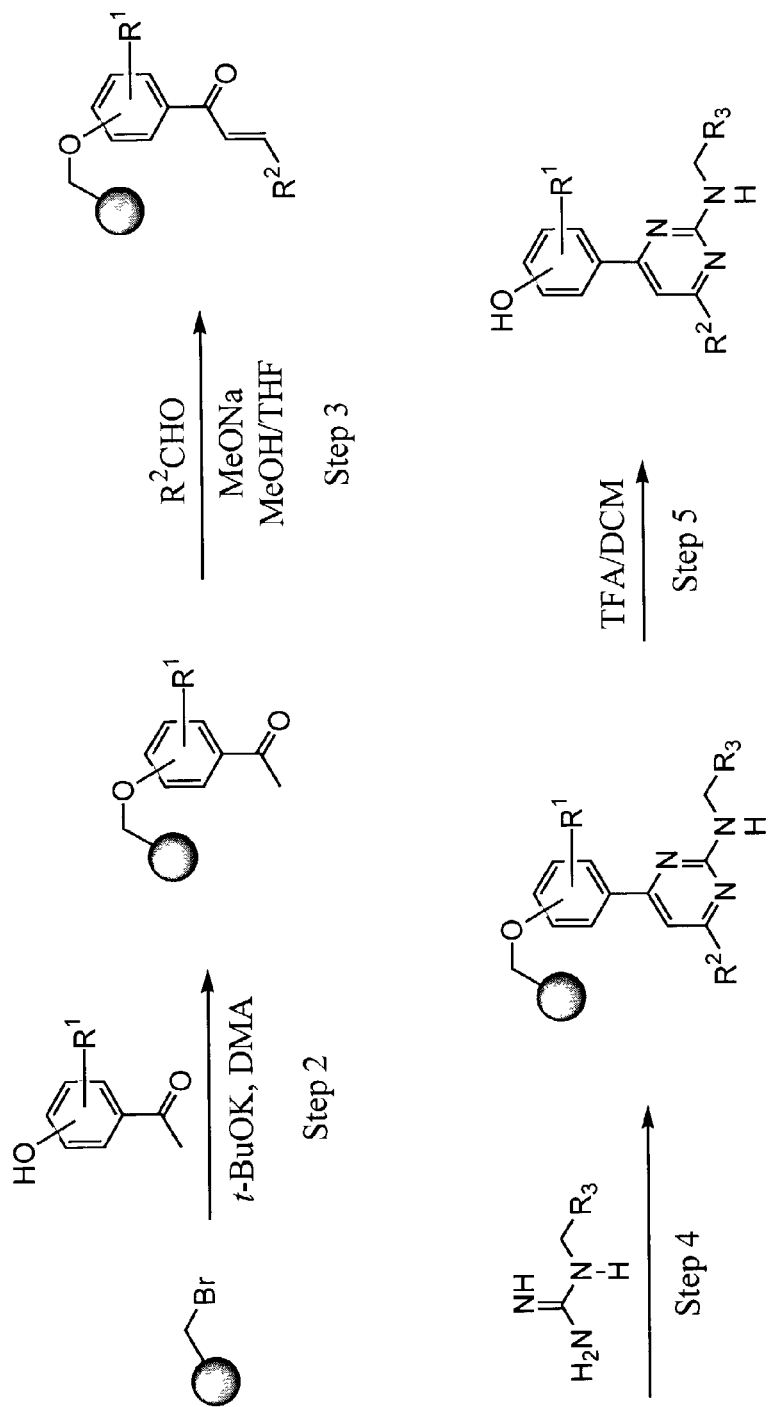
FIG. 1 shows the synthesis of the compounds according to the invention as also described in Example 2.

The invention provides for compounds of the formula (1), or pharmaceutical acceptable salts or solvates thereof, hereinafter also referred to as the "compounds according to the invention" including particular and preferred embodiments thereof.

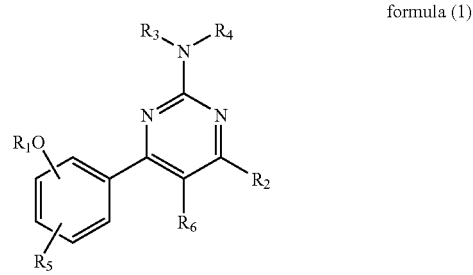

formula (1)

wherein in formula (1) as shown above, $R_1$ is hydrogen, $C_1$ to $C_7$ acyl or $C_1$ to $C_7$ substituted acyl;

$R_2$ is phenyl, substituted phenyl, $C_5$ to $C_6$ heteroaryl, $C_5$ to $C_6$ substituted heteroaryl, napthyl or substituted napthyl;

$R_3$ and $R_4$ are each independently hydrogen, $C_1$ to $C_8$ alkyl, $C_1$ to $C_8$ substituted alkyl, $C_7$ to $C_{12}$ alkylphenyl, or $C_7$ to $C_{12}$ substituted phenylalkyl, or $R_3$ and $R_4$ together with nitrogen form a heterocycle or substituted heterocycle, a heteroaryl, or substituted heteroaryl ring;

$R_5$ is hydrogen, $C_1$ to $C_8$ alkyl, halogen, $C_1$ to $C_8$ alkoxy, carboxy, ester, amide, susbstituted amide, or $C_1$ to $C_8$ aminoacyl; and $R_6$ is hydrogen, $C_1$ to $C_8$ alkyl, $C_1$ to $C_8$ substituted alkyl.

The compounds of the invention can also exist as solvates and hydrates. Thus, these compounds may crystallize with, for example, waters of hydration, or one, a number of, or any fraction thereof of molecules of the mother liquor solvent. The solvates and hydrates of such compounds are included within the scope of this invention. Also included within the scope of the invention are resolved diastereoisomers and enantiomers and tautomers.

The term "mammalian receptor homologue" of the protein according to SEQ ID NO. 1 as used herein is a protein that performs substantially the same task as NR1H4 does in humans and shares at least 40% sequence identity at the amino acid level, preferably 50% sequence identity at the amino acid level more preferably 65% sequence identity at the amino acid level, even more preferably 75% sequence identity at the amino acid level and most preferably over 85% sequence identity at the amino acid level.

The term "halogen" refers to the fluoro, chloro, bromo or iodo atoms. There can be one or more halogen, which are the same or different. Preferred halogens are chloro and fluoro.

The term "$C_1$ to $C_7$ acyl" encompasses groups such as formyl, acetyl, propionyl, butyryl, pentanoyl, pivaloyl, hexanoyl, heptanoyl, benzoyl, and the like. Preferred acyl groups are acetyl and benzoyl.

The term "$C_1$ to $C_7$ substituted acyl" denotes the acyl group substituted by one or more, and preferably one or two, halogen, hydroxy, protected hydroxy, oxo, protected oxo, cyclohexyl, naphthyl, amino, protected amino, monosubstituted amino, protected monosubstituted amino, disubstituted amino, guanidino, heterocyclic ring, substituted heterocyclic ring, imidazolyl, indolyl, pyrrolidinyl, $C_1$ to $C_7$ alkoxy, $C_1$ to $C_7$ acyl, $C_1$ to $C_7$ acyloxy, nitro, $C_1$ to $C_6$ alkyl ester, carboxy, protected carboxy, carbamoyl, carboxamide, protected carboxamide, N-($C_1$ to $C_6$ alkyl)carboxamide, protected N-($C_1$ to $C_6$ alkyl)carboxamide, N,N-di($C_1$ to $C_6$ alkyl)carboxamide, cyano, methylsulfonylamino, thiol, $C_1$ to $C_4$ alkylthio or $C_1$ to $C_4$ alkylsulfonyl groups. The substituted acyl groups may be substituted once or more, and preferably once or twice, with the same or with different substituents.

Examples of $C_1$ to $C_7$ substituted acyl groups include 4-phenylbutyroyl, 3-phenylbutyroyl, 3-phenylpropanoyl, 2-cyclohexanylacetyl, cyclohexanecarbonyl, 2-furanoyl, 3-dimethylaminobenzoyl, and the like.

The term "substituted phenyl" specifies a phenyl group substituted with one or more, and preferably one or two, moieties chosen from the groups consisting of halogen, hydroxy, protected hydroxy, cyano, nitro, $C_1$ to $C_6$ alkyl, $C_1$ to $C_6$ substituted alkyl, $C_1$ to $C_7$ alkoxy, $C_1$ to $C_7$ substituted alkoxy, $C_1$ to $C_7$ acyl, $C_1$ to $C_7$ substituted acyl, $C_1$ to $C_7$ acyloxy, carboxy, protected carboxy, carboxymethyl, protected carboxymethyl, hydroxymethyl, protected hydroxymethyl, amino, protected amino, monosubstituted amino, protected monosubstituted amino, disubstituted amino, carboxamide, protected carboxamide, N-($C_1$ to $C_6$ alkyl) carboxamide, protected N-($C_1$ to $C_6$ alkyl)carboxamide, N,N-di($C_1$ to $C_6$ alkyl)carboxamide, trifluoromethyl, N-(($C_1$ to $C_6$ alkyl)sulfonyl)amino, N-(phenylsulfonyl)amino or phenyl, wherein the phenyl is substituted or unsubstituted, such that, for example, a biphenyl results.

Examples of the term "substituted phenyl" include a mono- or di(halo)phenyl group such as 2, 3 or 4-chlorophenyl, 2,6-dichlorophenyl, 2,5-dichlorophenyl, 3,4-dichlorophenyl, 2, 3 or 4-bromophenyl, 3,4-dibromophenyl, 3-chloro-4-fluorophenyl, 2, 3 or 4-fluorophenyl and the like; a mono or di(hydroxy)phenyl group such as 2, 3 or 4-hydroxyphenyl, 2,4-dihydroxyphenyl, the protected-hydroxy derivatives thereof and the like; a nitrophenyl group such as 2, 3 or 4-nitrophenyl; a cyanophenyl group, for example, 2, 3 or 4-cyanophenyl; a mono- or di(alkyl)phenyl group such as 2, 3 or 4-methylphenyl, 2,4-dimethylphenyl, 2, 3 or 4-(isopropyl)phenyl, 2, 3 or 4-ethylphenyl, 2, 3 or 4-(n-propyl)phenyl and the like; a mono or di(alkoxyl)phenyl group, for example, 2,6-dimethoxyphenyl, 2, 3 or 4-methoxyphenyl, 2, 3 or 4-ethoxyphenyl, 2, 3 or 4-(isopropoxy) phenyl, 2, 3 or 4-(t-butoxy)phenyl, 3-ethoxy-4-methoxyphenyl and the like; 2, 3 or 4-trifluoromethylphenyl; a mono- or dicarboxyphenyl or (protected carboxy)phenyl group such as 2, 3 or 4-carboxyphenyl or 2,4-di(protected carboxy) phenyl; a mono-or di(hydroxymethyl)phenyl or (protected hydroxymethyl)phenyl such as 2, 3, or 4-(protected hydroxymethyl)phenyl or 3,4-di(hydroxymethyl)phenyl; a mono- or di(aminomethyl)phenyl or (protected aminomethyl)phenyl such as 2, 3 or 4-(aminomethyl)phenyl or 2,4-(protected aminomethyl)phenyl; or a mono- or di(N-(methylsulfonylamino))phenyl such as 2, 3 or 4-(N-(methylsulfonylamino))phenyl. Also, the term "substituted phenyl" represents disubstituted phenyl groups wherein the substituents are different, for example, 3-methyl-4-hydroxyphenyl, 3-chloro-4-hydroxyphenyl, 2-methoxy-4-bromophenyl, 4-ethyl-2-hydroxyphenyl, 3-hydroxy-4-nitrophenyl, 2-hydroxy 4-chlorophenyl, and the like.

The term "heteroaryl" means a heterocyclic aromatic derivative, which is a five-membered or six-membered ring system having from 1 to 4 heteroatoms, such as oxygen, sulfur and/or nitrogen, in particular nitrogen, either alone or in conjunction with sulfur or oxygen ring atoms. Examples of heteroaryls include pyridinyl, pyrimidinyl, and pyrazinyl, pyridazinyl, pyrrolo, furano, thiopheno, oxazolo, isoxazolo, phthalimido, thiazolo, and the like.

The term "substituted heteroaryl" means the above-described heteroaryl is substituted with, for example, one or more, and preferably one or two, substituents which are the same or different which substituents can be halogen, hydroxy, protected hydroxy, cyano, nitro, $C_1$ to $C_6$ alkyl, $C_1$ to $C_7$ alkoxy, $C_1$ to $C_7$ substituted alkoxy, $C_1$ to $C_7$ acyl, $C_1$ to $C_7$ substituted acyl, $C_1$ to $C_7$ acyloxy, carboxy, protected carboxy, carboxymethyl, protected carboxymethyl, hydroxymethyl, protected hydroxymethyl, amino, protected amino, monosubstituted amino, protected monosubstituted amino, disubstituted amino, carboxamide, protected carboxamide, N-($C_1$ to $C_6$ alkyl)carboxamide, protected N-($C_1$ to $C_6$ alkyl)carboxamide, N,N-di($C_1$ to $C_6$ alkyl)carboxamide, trifluoromethyl, N-(($C_1$ to $C_6$ alkyl)sulfonyl)amino or N-(phenylsulfonyl)amino groups.

The term "substituted naphthyl" specifies a naphthyl group substituted with one or more, and preferably one or two, moieties either on the same ring or on different rings chosen from the groups consisting of halogen, hydroxy, protected hydroxy, cyano, nitro, $C_1$ to $C_6$ alkyl, $C_1$ to $C_7$ alkoxy, $C_1$ to $C_7$ acyl, $C_1$ to $C_7$ acyloxy, carboxy, protected carboxy, carboxymethyl, protected carboxymethyl, hydroxymethyl, protected hydroxymethyl, amino, protected amino, monosubstituted amino, protected monosubstituted amino, disubstituted amino, carboxamide, protected carboxamide, N-($C_1$ to $C_6$ alkyl)carboxamide, protected N-($C_1$ to $C_6$ alkyl)carboxamide, N,N-di($C_1$ to $C_6$ alkyl)carboxamide, trifluoromethyl, N-(($C_1$ to $C_6$ alkyl)sulfonyl)amino, or N-(phenylsulfonyl)amino.

Examples of the term "substituted naphthyl" includes a mono or di(halo)naphthyl group such as 1, 2, 3, 4, 5, 6, 7 or 8-chloronaphthyl, 2,6-dichloronaphthyl, 2,5-dichloronaphthyl, 3,4-dichloronaphthyl, 1, 2, 3, 4, 5, 6, 7 or 8-bromonaphthyl, 3,4-dibromonaphthyl, 3-chloro-4-fluoronaphthyl, 1, 2, 3, 4, 5, 6, 7 or 8-fluoronaphthyl and the like; a mono or di(hydroxy)naphthyl group such as 1, 2, 3, 4, 5, 6, 7 or 8-hydroxynaphthyl, 2,4-dihydroxynaphthyl, the protected-hydroxy derivatives thereof and the like; a nitronaphthyl group such as 3- or 4-nitronaphthyl; a cyanonaphthyl group, for example, 1, 2, 3, 4, 5, 6, 7 or 8-cyanonaphthyl; a mono- or di(alkyl)naphthyl group such as 2, 3, 4, 5, 6, 7 or 8-methylnaphthyl, 1,2,4-dimethylnaphthyl, 1, 2, 3, 4, 5, 6, 7 or 8-(isopropyl)naphthyl, 1, 2, 3, 4, 5, 6, 7 or 8-ethylnaphthyl, 1, 2, 3, 4, 5, 6, 7 or 8-(n-propyl)naphthyl and the like; a mono or di(alkoxy)naphthyl group, for example, 2,6-dimethoxynaphthyl, 1, 2, 3, 4, 5, 6, 7 or 8-methoxynaphthyl, 1, 2, 3, 4, 5, 6, 7 or 8-ethoxynaphthyl, 1, 2, 3, 4, 5, 6, 7 or 8-(isopropoxy)naphthyl, 1, 2, 3, 4, 5, 6, 7 or 8-(t-butoxy)naphthyl, 3-ethoxy-4-methoxynaphthyl and the like; 1, 2, 3, 4, 5, 6, 7 or 8-trifluoromethylnaphthyl; a mono- or dicarboxynaphthyl or (protected carboxy)naphthyl group such as 1, 2, 3, 4, 5, 6, 7 or 8-carboxynaphthyl or 2,4-di(-protected carboxy)naphthyl; a mono- or di(hydroxymethyl)naphthyl or (protected hydroxymethyl)naphthyl such as 1, 2, 3, 4, 5, 6, 7 or 8-(protected hydroxymethyl)naphthyl or 3,4-di(hydroxymethyl)naphthyl; a mono- or di(amino)naphthyl or (protected amino)naphthyl such as 1, 2, 3, 4, 5, 6, 7 or 8-(amino)naphthyl or 2,4-(protected amino)-naphthyl, a mono- or di(aminomethyl)naphthyl or (protected aminomethyl)naphthyl such as 2, 3, or 4-(aminomethyl)naphthyl or 2,4-(protected aminomethyl)-naphthyl; or a mono- or di-(N-methylsulfonylamino) naphthyl such as 1, 2, 3, 4, 5, 6, 7 or 8-(N-methylsulfonylamino)naphthyl. Also, the term "substituted naphthyl" represents disubstituted naphthyl groups wherein the substituents are different, for example, 3-methyl-4-hydroxynaphth-1-yl, 3-chloro-4-hydroxynaphth-2-yl, 2-methoxy-4-bromonaphth-1-yl, 4-ethyl-2-hydroxynaphth-1-yl, 3-hydroxy-4-nitronaphth-2-yl, 2-hydroxy-4-chloronaphth-1-yl, 2-methoxy-7-bromonaphth-1-yl, 4-ethyl-5-hydroxynaphth-2-yl, 3-hydroxy-8-nitronaphth-2-yl, 2-hydroxy-5-chloronaphth-1-yl, and the like.

The term "$C_1$ to $C_8$ alkyl" denotes such radicals as methyl, ethyl, n-propyl, isopropyl, n-butyl, iso-butyl, sec-butyl, tert-butyl, amyl, tert-amyl, hexyl, n-heptyl, 2-heptyl, 3-heptyl, 4-heptyl, 2-methyl-1hexyl, 2-methyl-2hexyl, 2-methyl-3-hexyl, n-octyl, and the like.

Examples of the above substituted alkyl groups include the 2-oxo-prop-1-yl, 3-oxo-but-1-yl, cyanomethyl, nitromethyl, chloromethyl, hydroxymethyl, tetrahydropyranyloxymethyl, trityloxymethyl, propionyloxymethyl, amino, methylamino, aminomethyl, dimethylamino, carboxymethyl, allyloxycarbonylmethyl, allyloxycarbonylaminomethyl, methoxymethyl, ethoxymethyl, t-butoxymethyl, acetoxymethyl, chloromethyl, bromomethyl, iodomethyl, trifluoromethyl, 6-hydroxyhexyl, 2,4-dichloro(n-butyl), 2-aminopropyl, 1-chloroethyl, 2-chloroethyl, 1-bromoethyl, 2-chloroethyl, 1-fluoroethyl, 2-fluoroethyl, 1-iodoethyl, 2-iodoethyl, 1-chloropropyl, 2-chloropropyl, 3-chloropropyl, 1-bromopropyl, 2-bromopropyl, 3-bromopropyl, 1-fluoropropyl, 2-fluoropropyl, 3-fluoropropyl, 1-iodopropyl, 2-iodopropyl, 3-iodopropyl, 2-aminoethyl, 1-aminoethyl, N-benzoyl-2-aminoethyl, N-acetyl-2-aminoethyl, N-benzoyl-1-aminoethyl, N-acetyl-1-aminoethyl, and the like.

The term "$C_1$ to $C_8$ substituted alkyl" denotes that the above $C_1$ to $C_8$ alkyl groups are substituted by one or more, and preferably one or two, halogen, hydroxy, protected hydroxy, oxo, protected oxo, $C_3$ to $C_7$ cycloalkyl, naphthyl, amino, protected amino, monosubstituted amino, protected monosubstituted amino, disubstituted amino, guanidino, protected guanidino, heterocyclic ring, substituted heterocyclic ring, imidazolyl, indolyi, pyrrolidinyl, $C_1$ to $C_7$ alkoxy, $C_1$ to $C_7$ acyl, $C_1$ to $C_7$ acyloxy, nitro, carboxy, protected carboxy, carbamoyl, carboxamide, protected carboxamide, N-($C_1$ to $C_6$ alkyl)carboxamide, protected N-($C_1$ to $C_6$ alkyl)carboxamide, N,N-di($C_1$ to $C_6$ alkyl)carboxamide, cyano, methylsulfonylamino, thiol, $C_1$ to $C_4$ alkylthio or $C_1$ to $C_4$ alkylsulfonyl groups. The substituted alkyl groups may be substituted once or more, and preferably once or twice, with the same or with different substituents.

The term "$C_7$ to $C_{12}$ phenylalkyl" denotes a $C_1$ to $C_6$ alkyl group substituted at any position by a phenyl, substituted phenyl, heteroaryl or substituted heteroaryl. Examples of such a group include benzyl, 2-phenylethyl, 3-phenyl(n-propyl), 4-phenylhexyl, 3-phenyl(n-amyl), 3-phenyl(sec-butyl), and the like. Preferred $C_7$ to $C_{12}$ phenylalkyl groups are the benzyl and the phenylethyl groups.

The term "$C_7$ to $C_{12}$ substituted phenylalkyl" denotes a $C_7$ to $C_{12}$ phenylalkyl group substituted on the $C_1$ to $C_6$ alkyl portion with one or more, and preferably one or two, groups chosen from halogen, hydroxy, protected hydroxy, oxo, protected oxo, amino, protected amino, monosubstituted amino, protected monosubstituted amino, disubstituted amino, guanidino, protected guanidino, heterocyclic ring, substituted heterocyclic ring, $C_1$ to $C_6$ alkyl, $C_1$ to $C_6$ substituted alkyl, $C_1$ to $C_7$ alkoxy, $C_1$ to $C_7$ substituted alkoxy, $C_1$ to $C_7$ acyl, $C_1$ to $C_7$ substituted acyl, $C_1$ to $C_7$ acyloxy, nitro, carboxy, protected carboxy, carbamoyl, carboxamide, protected carboxamide, N-($C_1$ to $C_6$ alkyl)carboxamide, protected N-($C_1$ to $C_6$ alkyl)carboxamide, N,N-($C_1$ to $C_6$ dialkyl)carboxamide, cyano, N-($C_1$ to $C_6$ alkylsulfonyl)amino, thiol, $C_1$ to $C_4$ alkylthio, $C_1$ to $C_4$ alkylsulfonyl groups; and/or the phenyl group may be substituted with one or more, and preferably one or two, substituents chosen from halogen, hydroxy, protected hydroxy, cyano, nitro, $C_1$ to $C_6$ alkyl, $C_1$ to $C_6$ substituted alkyl, $C_1$ to $C_7$ alkoxy, $C_1$ to $C_7$ substitute alkoxy, $C_1$ to $C_7$ acyl, $C_1$ to $C_7$ substituted acyl, $C_1$ to $C_7$ acyloxy, carboxy, protected carboxy, carboxymethyl, protected carboxymethyl, hydroxymethyl, protected hydroxymethyl, amino, protected amino, monosubstituted amino, protected monosubstituted amino, disubstituted amino, carboxamide, protected carboxamide, N-($C_1$ to $C_6$ alkyl) carboxamide, protected N-($C_1$ to $C_6$ alkyl) carboxamide, N,N-di($C_1$ to $C_6$ alkyl)carboxamide, trifluoromethyl, N-(($C_1$ to $C_6$ alkyl)sulfonyl)amino, N-(phenylsulfonyl)amino, cyclic $C_2$ to $C_7$ alkylene or a phenyl group, substituted or unsubstituted, for a resulting biphenyl group. The substituted alkyl or phenyl groups may be substituted with one or more, and preferably one or two, substituents which can be the same or different.

Examples of the term "$C_7$ to $C_{12}$ substituted phenylalkyl" include groups such as 2-phenyl-1-chloroethyl, 2-(4-methoxyphenyl)ethyl, 4-(2,6-dihydroxy phenyl)n-hexyl, 2-(5-cyano-3-methoxyphenyl)n-pentyl, 3-(2,6-dimethylphenyl)n-propyl, 4-chloro-3-aminobenzyl, 6-(4-methoxyphenyl)-3-carboxy(n-hexyl), 5-(4-aminomethylphenyl)-3-(aminomethyl)n-pentyl, 5-phenyl-3-oxo-n-pent-1-yl, and the like.

As outlined above $R_3$ and $R_4$ may be taken together with nitrogen to form a heterocycle or substituted heterocycle of the following kind aziridine, azetidine, pyrrolidine, 3-methylpyrrolidine, 3-aminopyrrolidine, 3-hydroxypyrrolidine, pyrazolidine, imidazolidine, piperidine, 2-methylpiperidine, piperazine, morpholine, azepine, and tetrahydroisoquinoline.

The term "heterocycle" or "heterocyclic ring" denotes optionally substituted five-membered to eight-membered rings that have 1 to 4 heteroatoms, such as oxygen, sulfur and/or nitrogen, in particular nitrogen, either alone or in conjunction with sulfur or oxygen ring atoms. These five-membered to eight-membered rings may be saturated, fully unsaturated or partially unsaturated, with fully saturated rings being preferred. Preferred heterocyclic rings include morpholino, piperidinyl, piperazinyl, 2-amino-imidazoyl, tetrahydrofurano, pyrrolo, tetrahydrothiophen-yl, hexylmethyleneimino and heptylmethyleneimino.

The term "substituted heterocycle" or "substituted heterocyclic ring" means the above-described heterocyclic ring is substituted with, for example, one or more, and preferably one or two, substituents which are the same or different which substituents can be halogen, hydroxy, protected hydroxy, cyano, nitro, $C_1$ to $C_{12}$ alkyl, $C_1$ to $C_{12}$ alkoxy, $C_1$ to $C_{12}$ substituted alkoxy, $C_1$ to $C_{12}$ acyl, $C_1$ to $C_{12}$ acyloxy, carboxy, protected carboxy, carboxymethyl, protected carboxymethyl, hydroxymethyl, protected hydroxymethyl, amino, protected amino, monosubstituted amino, protected monosubstituted amino, disubstituted amino carboxamide, protected carboxamide, N-($C_1$ to $C_{12}$ alkyl)carboxamide, protected N-($C_1$ to $C_{12}$ alkyl)carboxamide, N,N-di($C_1$ to $C_{12}$ alkyl)carboxamide, trifluoromethyl, N-(($C_1$ to $C_{12}$ alkyl)sulfonyl)amino, N-(phenylsulfonyl)amino, and heterocycle or substituted heterocycle groups.

The term "$C_1$ to $C_8$ alkoxy" as used herein denotes groups such as methoxy, ethoxy, n-propoxy, isopropoxy, n-butoxy, t-butoxy and like groups. A preferred alkoxy is methoxy. The term "$C_1$ to $C_8$ substituted alkoxy" means the alkyl portion of the alkoxy can be substituted in the same manner as in relation to $C_1$ to $C_8$ substituted alkyl.

The term "$C_1$ to $C_8$ aminoacyl" encompasses groups such as formyl, acetyl, propionyl, butyryl, pentanoyl, pivaloyl, hexanoyl, heptanoyl, octanoyl, benzoyl and the like.

The term "$C_1$ to $C_8$ substituted aminoacyl" denotes the acyl group substituted by one or more, and preferably one or two, halogen, hydroxy, protected hydroxy, oxo, protected oxo, cyclohexyl, naphthyl, amino, protected amino, monosubstituted amino, protected monosubstituted amino, disubstituted amino, guanidino, heterocyclic ring, substituted heterocyclic ring, imidazolyl, indolyl, pyrrolidinyl, $C_1$ to $C_{12}$ alkoxy, $C_1$ to $C_{12}$ acyl, $C_1$ to $C_{12}$ acyloxy, nitro, $C_1$ to $C_{12}$ alkyl ester, carboxy, protected carboxy, carbamoyl, carboxamide, protected carboxamide, N-($C_1$ to $C_{12}$ alkyl)carboxamide, protected N-($C_1$ to $C_{12}$ alkyl)carboxamide, N,N-di($C_1$ to $C_{12}$ alkyl)carboxamide, cyano, methylsulfonylamino, thiol, $C_1$ to $C_{10}$ alkylthio or $C_1$ to $C_{10}$ alkylsulfonyl groups. The substituted acyl groups may be substituted once or more, and preferably once or twice, with the same or with different substituents.

Examples of $C_1$ to $C_8$ substituted acyl groups include 4-phenylbutyroyl, 3-phenylbutyroyl, 3-phenylpropanoyl, 2-cyclohexanylacetyl, cyclohexanecarbonyl, 2-furanoyl and 3-dimethylaminobenzoyl.

This invention provides a pharmaceutical composition comprising an effective amount of a compound according to the invention. Such compounds can be administered by various routes, for example, oral, rectal, transdermal, subcutaneous, intramuscular, intravenous or intracerebral. The preferred route of administration would be oral at daily doses of the compound for adult human treatment of about 0.01 to 5000 mg, preferably 1 to 1500 mg per day. The appropriate dose may be administered as a single dose or as divided doses presented at appropriate intervals for example as two, three four or more subdoses per day.

For preparing pharmaceutical compositions containing compounds of the invention, inert, pharmaceutically acceptable carriers are used. The pharmaceutical carrier can be either solid or liquid. Solid form preparations include, for example, powders, tablets, dispersible granules, capsules, cachets, and suppositories.

A solid carrier can be one or more substances which can also act as diluents, flavoring agents, solubilizers, lubricants, suspending agents, binders, or tablet disintegrating agents; it can also be an encapsulating material.

In powders, the carrier is generally a finely divided solid which is in a mixture with the finely divided active component. In tablets, the active compound is mixed with the carrier having the necessary binding properties in suitable proportions and compacted in the shape and size desired.

For preparing pharmaceutical composition in the form of suppositories, a low-melting wax such as a mixture of fatty acid glycerides and cocoa butter is first melted and the active ingredient is dispersed therein by, for example, stirring. The molten homogeneous mixture is then poured into convenient-sized molds and allowed to cool and solidify.

Powders and tablets preferably contain between about 5% to about 70% by weight of the active ingredient. Suitable carriers include, for example, magnesium carbonate, magnesium stearate, talc, lactose, sugar, pectin, dextrin, starch, tragacanth, methyl cellulose, sodium carboxymethyl cellulose, a low-melting wax, cocoa butter and the like.

The pharmaceutical compositions can include the formulation of the active compound with encapsulating material as a carrier providing a capsule in which the active component (with or without other carriers) is surrounded by a carrier, which is thus in association with it. In a similar manner, cachets are also included. Tablets, powders, cachets, and capsules can be used as solid dosage forms suitable for oral administration.

Liquid pharmaceutical compositions include, for example, solutions suitable for oral or parenteral administration, or suspensions, and emulsions suitable for oral administration. Sterile water solutions of the active component or sterile solutions of the active component in solvents comprising water, ethanol, or propylene glycol are examples of liquid compositions suitable for parenteral administration.

Sterile solutions can be prepared by dissolving the active component in the desired solvent system, and then passing the resulting solution through a membrane filter to sterilize it or, alternatively, by dissolving the sterile compound in a previously sterilized solvent under sterile conditions.

In one embodiment of the present invention a compound is claimed according to formula (1) above, or pharmaceutical acceptable salts or solvates thereof, wherein $R_1$ is hydrogen, $R_2$ is substituted phenyl, $C_5$ to $C_6$ heteroaryl, or $C_5$ to $C_6$ substituted heteroaryl, $R_3$ is hydrogen, $R_4$ in formula (1) is a structure according to formula (2) shown below, $R_5$ is hydroben or a halogen, $R_6$ is hydrogen and $R_7$ is hydrogen.

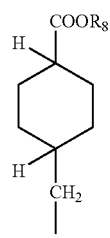

formula (2)

wherein the COOR$_8$ and the methylene substituents can adopt all possible diastereomeric configurations and R$_8$ is hydroben, methyl or ethyl.

In one preferred embodiment of the present invention a compound is claimed according to formula (1) above, or pharmaceutical acceptable salts or solvates thereof, wherein R$_1$ is hydrogen; R$_2$ is substituted phenyl, C$_5$ to C$_6$ heteroaryl, C$_5$ to C$_6$ substituted heteroaryl; R$_3$ is hydrogen; R$_4$ in formula (1) is a structure according to formula (3) shown below; R$_5$ is hydrogen or a halogen; and R$_6$ is hydrogen.

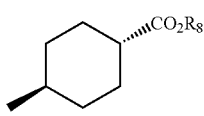

formula (3)

wherein the COOR$_8$ and the methylene substituents are in double axial (a,a) positions and R$_8$ is H, methyl or ethyl.

In a preferred embodiment of the invention a compound is claimed, or pharmaceutical acceptable salts or solvates thereof, wherein R$_1$ is hydrogen; R$_2$ is substituted phenyl; R$_3$ is hydrogen; R$_4$ in formula (1) is a structure according to formula (3) shown above; R$_5$ is hydrogen; and R$_6$ is hydrogen, R$_8$ is H, methyl or ethyl.

A particularly preferred compound which may act as agonist of NR1H4 is shown in formula (4) below. The compound according to formula (4) has a low effective concentration at FXR with an EC$_{50}$ of 0.16 μM wherein the EC$_{50}$ reflects the half-maximal effective concentration, and which is higher than the EC$_{50}$ of 0.015 μM for the published FXR agonist GW4064 (B. Goodwin et al., Molecular Cell 6, 517–526, 2000).

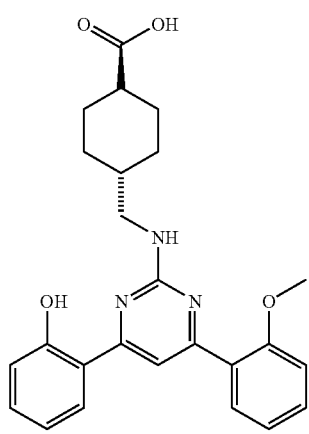

formula (4)

The compounds according to formula (5, 6, 7,) shown below are active as agonists of the NR1H4 human nuclear receptor.

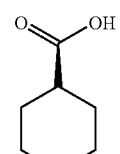

formula (5)

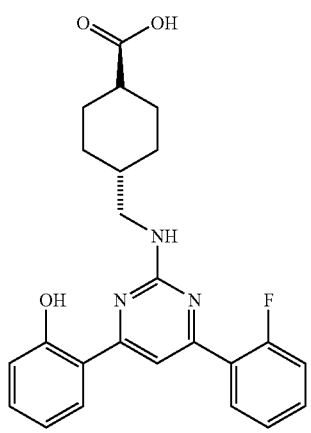

formula (6)

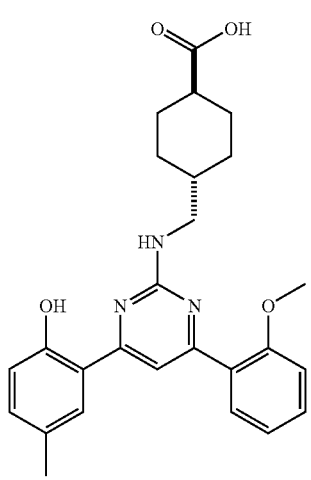

formula (7)

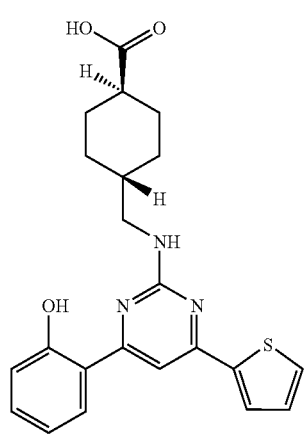

In particular the invention relates to a compound as described above wherein said compounds is capable of binding the NR1H4 receptor protein or a portion thereof according to SEQ ID NO. 1 (FIG. 2A) or a mammalian homologue thereof. The claimed compound can bind to the NR1H4 receptor protein or a portion thereof in a mixture comprising 10–200 ng of NR1H4 receptor protein or a portion thereof, preferably the ligand binding domain, 20 mM Tris/HCl at pH 7.9; 60 mM KCl; 5 mM MgCl$_2$; 160 ng/μl BSA in a total volume of preferably about 25 μl.

Shown below are various known FXR ligands:

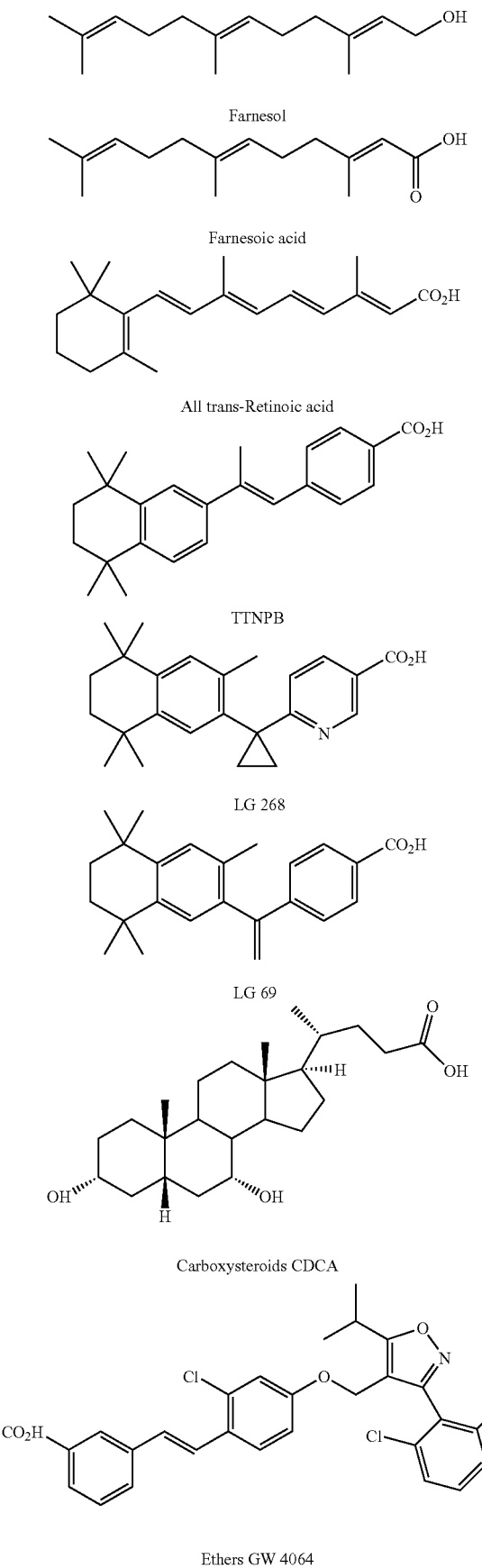

Farnesol

Farnesoic acid

All trans-Retinoic acid

TTNPB

LG 268

LG 69

Carboxysteroids CDCA

Ethers GW 4064

As can be seen the compounds of the present invention are structurally unrelated to these known ligands.

The invention in particular concerns a method for prevention or treatment of a NR1H4 receptor protein or NR1H4 receptor protein homologue mediated disease or condition in a mammal comprising administration of a therapeutically effective amount of a compound according to the invention wherein the prevention or treatment is directly or indirectly accomplished through the binding of a compound according to the invention to the NR1H4 receptor protein or to the NR1H4 receptor protein homologue.

The term mediated herein means that the physiological pathway in which the NR1H4 receptor protein acts is either directly or indirectly involved in the disease or condition to be treated or prevented. In the case where it is indirectly involved it could be that, e.g. modulating the activity of NR1H4 by a compound according to the invention influences a parameter which has a beneficial effect on a disease or a condition. One such example is that modulation of NR1H4 activity leads to decreased levels of serum cholesterol or certain lipoproteins which in turn have a beneficial effect on the prevention and treatment of artherosclerosis. Herein a condition is a physiological or phenotypic state which is desirably altered. Another example would be the treatment of cholestatic conditions in which bile flow from the liver to the gut is impaired which results in a tailback of toxic metabolites to the liver. Cholestasis can be a primary condition where bile flow is directly impaired or a secondary condition where a primary impairment in liver function such as liver cirrhosis results in a secondary cholestasis. Agonists that activate NR1H4 resulting in increased bile acid export from the hpeatocyte into the liver canaliculi and subsequent increased bile flow might be used for the treatment of these different types of cholestasis.

In a preferred embodiment of the invention the method for prevention or treatment of a NR1H4 receptor protein mediated disease or condition is applied to a human. This may be male or female.

Listed below are various genes that have been found to be regulated in mammalians by binding of an FXR agonist to the FXR receptor.

Genes Down-Regulated in Liver:
Apolipoprotein A1, ApoA1 (NM000039), plasma proteinase inhibitor alpha-1-inhibitor III group 3(m22360), L-glucono-gamma-lactone oxidase (d12754), Peroxisomal enoyl-CoA:hydrotase-3-hydroxyacyl-CoA bifunctional enzyme (k03249) liver fatty acid binding protein (L-FABP, m13501), CYP4A2(m57719, CYP3A23 (x96721), CYP3A1 (x64401);(b), Cholesterol-7-alpha-hydroxylase, CYP7A1 (RefSeq NM000780, XM 005022, XM 044651, XM 044652), Sodium-taurocholate cotransport protein, ntcp (RefSeq NM003049, XM007466), CYP8B1 (NM004391).

Genes Up-Regulated in Liver:
Small heterodimer partner homolog (d86580), Bile salt export pump, bsep (RefSeq NM 003742, XM 003644, XM 033122), Phospholipid transfer protein, PLTP (RefSeq NM 006227, XM 009490, XM 029929, XM 029930), Carnitine palmitoyltransferase II, CPTII (RefSeq NM 000098, XM 001758, XM 038866, XM 038867), Phenylethanolamine-N-methyltransferase, PNMT (RefSeq NM 002686, XM 008597, XM 049837), insulin-induced growth-response protein CL-6 (I13619), elongation factor 2, EF-2 (y07504), mouse cornichon, protein kinase C receptor (u03390), mitochondrial cytochrome c oxidase (m27315), cystathione gamma-lyase (x53460, d17370), cytosolic phosphoenolypyruvate carboxykinase (k03243), histidase (m58308) S-adenosylmethionine synthetase (x60822), lanosterol 14-alpha-demethylase (u17697), G protein-coupled purinoceptor P2U (146865), hepatic squalene synthetase (m95591), ATP-binding cassette transporter, ABCC2 (Q92887), Apolipoprotein CII, APOCII (NM000483), Dehydroepiandrosterone sulfotransferase (XM049895).

Genes Regulated in the Intestine:

lipase (x61925), pancreatic lipase (d88534), colipase (m58370), pancreatic phospholipase A-2 (d00036), pancreatic amylase (m24962), carboxypeptidase AI (m23986), carboxypeptidase A2 (m23721), carboxypeptidase B (m23959), pancreatic trypsin I (j00778), pancreatic cationic trypsinogen (m16624), pancreatic trypsinogen II (v01274), elastase I (v01234, I00112), elastase II (I00118, I00124), I-BABP (I22788), intestinal fatty acid binding protein (FABP, k01180), hepatic squalenesynthetase (m95591), protein kinase C receptor (u003390), elongation factor 2, EF-2 (y07504), Small heterodimer partner homolog (d86580).

Pharmaceutical compositions generally are administered in an amount effective for treatment or prophylaxis of a specific condition or conditions. Initial dosing in human is accompanied by clinical monitoring of symptoms, such symptoms for the selected condition. In general, the compositions are administered in an amount of active agent of at least about 100 µg/kg body weight. In most cases they will be administered in one or more doses in an amount not in excess of about 20 mg/kg body weight per day. Preferably, in most cases, doses is from about 100 µg/kg to about 5 mg/kg body weight, daily.

For administration particularly to mammals, and particularly humans, it is expected that the daily dosage level of active agent will be 0.1 mg/kg to 10 mg/kg and typically around 1 mg/kg.

By "therapeutically effective amount" is meant a symptom-alleviating or symptom-reducing amount, a cholesterol-reducing amount, an amount that overcomes cholestatic conditions, a protein and/or carbohydrate digestion-blocking amount and/or a de novo cholesterol biosynthesis-blocking amount of a compound according to the invention.

FXR is proposed to be a bile acid sensor. As a result, it modulates both, the synthetic output of bile acids from the liver and their recycling in the intestine, by regulating bile acid binding proteins. In one embodiment of the invention the invention concerns a method for regulating the bile transport system in a mammal, in a preferred embodiment a human, which comprises activating the NR1H4 receptor with a therapeutically effective amount of a compound according to the invention.

Likewise the invention concerns a method of treating in mammal a disease which is affected by cholesterol, triglyceride, bile acid levels or bile flow comprising administering to a mammal in need of such treatment a therapeutically effective amount of a compound according to the invention.

Accordingly, the compounds according to the invention may also be used as a method of prevention or treatment of mammalian atherosclerosis, gallstone disease (cholelithiasis), primary and secondary forms of cholestasis, lipid disorders, obesity or cardiovascular disorders such as coronary heart disease or stroke.

The invention further concerns a method of blocking in a mammal the cholesterol absorption in the intestine of a mammal in need of such blocking comprising administering to a mammal in need of such treatment a therapeutically effective amount of a compound according to the invention. The invention may also be used to treat obesity in humans.

The Farnesoid X Receptor alpha is a prototypical type 2 nuclear receptor which activates genes upon binding to the promoter region of target genes in a heterodimeric fashion with Retinoid X Receptor. The relevant physiological ligands of NR1H4 are bile acids. The present compounds according to the invention have been demonstrated to have a high binding efficacy as measured as IC50 in the range 400 nM to 1000 nM as well as agonistic and/or antagonistic properties. Consequently they may be applied to regulate genes that participate in bile acid homeostasis as well as other downstream regulated genes. Examples of physiological functions in which such genes are involved are but are not limited to lipid absorption, cholesterol biosynthesis, cholesterol transport or binding, bile acid synthesis, bile acid transport or binding, proteolysis, amino acid metabolism, glucose biosynthesis, protein translation, electron transport, and hepatic fatty acid metabolism. FXR often functions in vivo as a heterodimer with the Retinoid X Receptor. Published FXR agonists such as the Glaxo SmithKline compound "GW 4064" and published FXR antagonists such as guggulsterone [4,17(20)-pregnadiene-3,16-dione] are known to influence the regulation of various liver genes. Genes found to be regulated by GW 4064 can be found in FIG. 6. Thus, the invention also concerns a method of modulating a gene whose expression is regulated by the NR1H4 receptor in a mammal comprising administration of a therapeutically effective amount of a compound according to the invention to said mammal.

It is known that the orphan receptor FXR can bind the response element of the shp gene as a heterodimer with RXR (9-cis retinoic acid receptor) and the SHP-protein, in turn, prevents efficient transcription from the cyp7a1 promoter (Lu et al., Mol Cell, 6(3):505–17; Goodwin et al. Mol Cell, 6(3), 717–26, 2000). Another gene that is repressed via SHP upon FXR activation is the Sodium/Bile Acid Cotransporter gene ntcp, a membrane transport protein which is required for the import of conjugated bile acids into the hepatocyte (Denson et al., Gastroenterology; 121(1):218–20, 2001). The gene for the Bile Salt Export Pump, a membrane transporter responsible for the secretion of bile acids into the gall is directly activated by FXR (Ananthanarayanan et al., J Biol Chem, 3; 276(31):28857–28865, 2001). Consequently, the invention likewise concerns a method for lowering the expression of cholesterol 7-alpha-hydroxylase and NTCP and increasing expression of BSEP and/or MDR2 (=multidrug resistance protein 2) in parallel by use of the compounds according to the invention. This is believed to be the ideal profile of an anti-cholestatic compound (Kullack-Ublick, et al., J Hepatol (2000) 32 Suppl 1:3–18). In one embodiment the invention concerns a method for enhancing the expression of the Intestinal Bile Acid Binding Protein (I-BABP) (Grober et al., J Biol Chem, 15; 274(42):29749–54, (1999) and/or the activity of the canicular bile salt excretion pump.

The compounds according to the invention may be used as medicaments, in particular for the manufacture of a medicament for the prevention or treatment of a NR1H4 receptor protein or NR1H4 receptor protein homologue mediated disease or condition in a mammal wherein the prevention or treatment is directly or indirectly accomplished through the binding of the compound according to the invention to the NR1H4 receptor protein or NR1H4 receptor protein homologue. These pharmaceutical compositions contain 0.1% to 99.5% of the compound according to the invention, more particularly 0.5% to 90% of the compound according to the invention in combination with a pharmaceutically acceptable carrier.

The invention concerns also the use of a compound according to the invention for the manufacture of a medicament for the prevention or treatment of a NR1H4 receptor protein mediated disease or condition wherein the mammal described above is a human. The medicament may be used for regulating the bile transport system in a mammal preferentially a human by activating the NR1H4 receptor, for regulating levels of cholesterol, triglyceride, bile acids and bile flow in mammals, preferentially humans. The medicament may be used for the treatment of atherosclerosis, gallstone disease (cholelithiasis), cholestasis, lipid disorders, obesity or a cardiovascular disorder.

The further concerns the use of a compound according to the invention for the manufacture of a medicament capable for blocking in a mammal, preferentially a human the cholesterol absorption in the intestine. Further the claimed compound may be used for the manufacture of a medicament for treating obesity in humans and for modulating a gene whose expression is regulated by the NR1H4 receptor (see details above and figures). The invention further concerns the use of a compound according to the invention for the manufacture of anticancer medicaments. The anticancer effects of such medicaments could be excerted by selective inhibition of cell proliferation and induction of apoptosis of tumor cells in a way similar to described activities for certain bisphosphonates (Alberts D S, et al., Clin Cancer Res 2001 May; 7(5): 1246–50)

EXAMPLE 1

In vitro Screening for Compounds which Influence FXR Binding to Coactivators

For screening purposes a fragment of the open reading frame of human FXR alpha (NR1H4-(Acc. No: AF384555)) encoding aminoacids 187–472 was amplified by standard RT PCR procedures (see figures; SEQ ID NO. 1 and 2). Starting material was total RNA derived from human liver. The resulting cDNA obtained after reverse transcription was subsequently cloned using the Gateway™ recombination technology (Invitrogen, USA) into the expression plasmid pDest15 (Invitrogen, USA). This construct was used to express a recombinant GST-FXR fusion protein in *E. coli* (BL21 strain). A pDEST 17 derivative clone harboring an additional sequence encoding amino acids 548–878 of human TIF2 (Acc. No: XM_011633 RefSeq) was constructed using Gateway™ recombination technology (Invitrogen, USA) in order to obtain a construct which was used to express recombinant His-tagged TIF2 fragment could be expressed in *E. coli*. For *E. coli* expression of both constructs, plasmid DNA was transformed into chemically competent *E. coli* BL21 (Invitrogen, USA) and cells were grown to an OD600 of 0.4–0.7 before expression was induced by addition of 0.5 mM IPTG according instructions of the manufacturer (Invitrogen). After induction for 8 hours at 30° C. cells were harvested by centrifugation for 10 minutes at 5000×g. Fusion proteins were affinity purified using Glutathion sepharose (Pharmacia) or Ni-NTA Agarose (QIAGEN) according to the instructions of the respective manufacturer. Recombinant proteins were dialyzed against 20 mM Tris/HCL pH 7.9; 60 mM KCl; 5 mM $MgCl_2$; 1 mM DTT, 0.2 mM PMSF; 10% glycerol. The TIF2 fragment was subsequently biotinylated by addition of 40–120 µl of a Biotinamidocaproate N-Hydroxysuccinimide-ester (Sigma) solution (20 mg/ml in DMSO). Overhead rotating samples were incubated for 2 hours at room temperature. Unincorporated label was then separated using G25 Gel filtration chromatography (Pharmacia Biotech, Sweden). Protein containing fractions from the column were pooled and tested for activity in the assay as described below.

For screening of compound libraries as provided for by the methods shown below in the examples for substances which influence the FXR/Tif 2 interaction, the Perkin Elmer LANCE technology was applied. This method relies on the binding dependent energy transfer from a donor to an acceptor fluorophore attached to the binding partners of interest. For ease of handling and reduction of background from compound fluorescence LANCE technology makes use of generic fluorophore labels and time resoved detection (for detailed description see Hemmilä I, Blomberg K and Hurskainen P, Time-resolved resonance energy transfer (TR-FRET) principle in LANCE, Abstract of Papers Presented at the 3 rd Annual Conference of the Society for Biomolecular Screening, September, California (1997).

For screening, 20–200 ng of biotinylated Tif 2 fragment and 10–200 ng of GST-FXR fragment were combined with 0.5–2 nM LANCE Eu-(W1024) labelled anti-GST antibody (Perkin Elmer) and 0.5–2 µg of Highly fluorescent APC-labelled streptavidin (Perkin Elmer) in the presence of 50 µM of individual compounds to be screened in a total volume of 25 µl of 20 mM Tris/HCl pH 7.9; 60 mM KCl; 5 mM $MgCl_2$; 160 ng/µl BSA. DMSO content of the samples was kept below 4%. Samples were incubated for a minimum of 60 minutes in the dark at room temperature in FIA-Plates black 384 well med. binding (Greiner).

The LANCE signal was detected by a Perkin Elmer VICTOR2V™ Multilabel Counter applying the detection parameters listed in Table 1 below. The results were visualized by plotting the ratio between the emitted light at 665 nm and at 615 nm. For every batch of recombinant proteins amount of proteins and labeling reagents giving the most sensitive detection of hits was determined individually by analysis of dose response curves for chenodeoxycholic acid.

TABLE 1

| Measurement parameters employed by a Wallace VICTOR2V ™ Multilabel Counter | |
|---|---|
| Number of repeats | 1 |
| plate: GREINER FIA-Plate black 384 well med. binding | |
| Measurement height | 3.50 mm |
| Label technology | TR-F Lance |
| Emission filter name | D615 |
| Emission filter slot | A1 |
| Emission aperture | Normal |
| Excitation filter | D340 |
| Delay | 50 µs |
| Window time | 400 µs |
| Cycle | 1000 µs |
| Light integrator capacitors | 1 |
| Light integrator ref. level | 95 |
| Flash energy area | High |
| Flash energy level | 223 |
| Flash absorbance measurement | No |
| Beam | Normal |
| Label technology | TR-F Lance |
| Emission filter name | D665 |
| Emission filter slot | A8 |
| Emission aperture | Normal |
| Excitation filter | D340 |
| Delay | 50 µs |
| Window time | 400 µs |
| Cycle | 1000 µs |
| Light integrator capacitors | 1 |
| Light integrator ref. level | 95 |
| Flash energy area | High |
| Flash energy level | 223 |
| Flash absorbance measurement | No |
| Beam | Normal |

EXAMPLE 2

Experimental Procedure for the Preparation of the Compounds According to the Invention Step 1. General procedure for preparation of Bromo-Wang resin: 2.0 g of Wang resin (1.28 mmol/g, 2.56 mmol) was placed in a porous polypropylene packet (Tea-bag, 60 mm×50 mm, 65µ), sealed and transferred to a 125 ml PP bottle. To this bottle was then added a freshly prepared solution of PPh$_3$Br$_2$ (3.24 g, 7.68 mmol, 3.0 eq, 0.15 M) in DCM (50 mL). After shaking at room temperature for 4–6 hours, the packet was washed with DCM (5×80 ml) and diethyl ether (4×80 ml). The packet was dried under vacuum overnight to afford off-white resin.

Step 2. Reaction of Acetophenones with Bromo-Wang resin: Each packet containing freshly prepared Bromo-Wang resin was transferred to an appropriate glass bottle, to which an acetophenone (25.6 mmol, 10 eq, 0.2 M), anhydrous DMA (125 ml) and KOtBu (3.14 g, 25.6 mmol, 10 eq, 0.2 M) were added sequentially. After shaking at 50° C. for 24 hours, the packet was washed alternatively with DMF (3×80 mL) and MeOH (2×80 ml) followed by DCM (2×80 ml) and MeOH (3×80 ml). The packet was air-dried overnight to afford off-white to pale brown resin, depending on the acetophenone used in the synthesis.

Step 3. Reaction of Aldehydes with Wang Resin-bound Acetophenones: Each packet of Acetophenone-Wang resin was transferred to a 250 mL PP bottle, to which a solution of NaOMe (51.2 mmol, 20 eq, 0.25 M) in 50% THF-MeOH (205 mL) and an aldehyde (51.2 mmol, 20 eq, 0.25 M) were added sequentially. After shaking at room temperature for 3 days, the packet was washed several times with MeOH (3×80 mL) and alternatively with DMF (80 mL) and MeOH (80 mL) for 3 cycles, followed by washes of DCM (2×80 mL) and MeOH (3×80 mL). The packet was air-dried overnight to afford a resin-bound Chalcone, that varied in color from yellow to dark red depending on the aldehyde used.

Step 4: Reaction of guanidines with the wang resin-bound chalcones. Each packet of chalcone-wang resin was transferred to a 250 ml glass bottle, to which was added a solution of naoet (51.2 mmol, 40 eq, 0.2 m) and guanidines (51.2 mmol, 20 eq, 0.2 m) in dmso (250 ml). after shaking at 80° C. for 18 hr, the packet was washed several times with meoh (3×80 ml) and alternatively with dmf (80 ml) and meoh (80 ml) for 3 cycles, followed by washes of dcm (2×80 ml) and meoh (3×80 ml). the packet was air-dried overnight to afford a resin-bound 2-aminopyrimidine derivative.

Step 5. Cleavage from Linker and Extraction: To a teabag containing approximately 50 mg of the resin, was added 2.5 mL of 20% TFA/DCM and it was shaken at room temperature for 2 hours. The teabag was then discarded and the excess solvent was removed on the Genevac evaporator. All of the final products were purified by preparation HPLC using ELSD detection to determine purity.

EXAMPLE 3

Determination of Dose Response of Compounds in Cellular Gene Reporter Assay

This example illustrates that a compound according to the invention can mediate transactivation of FXR mediated transcription in a HEK293 reporter cell line. Experiments shown were done with MOLSTRUCTURE LN 6691 (see structural formula below).

Stable HEK293-FXR reporter cell lines were generated by stably transfecting with the pTRexDest30 (Invitrogen) derivatives pTRexDest30-hFXR, pTRexDest30-hRXR and the pGL2promoter (Promega) derivative pGL2promoter-FXRRE. The full length human FXR (accession U68233) and the full length human RXRα (accession P19793) were cloned into the pTRexDest30 applying the manufacturer protocols for the Gateway™ system (Invitrogen).

Figure 3:
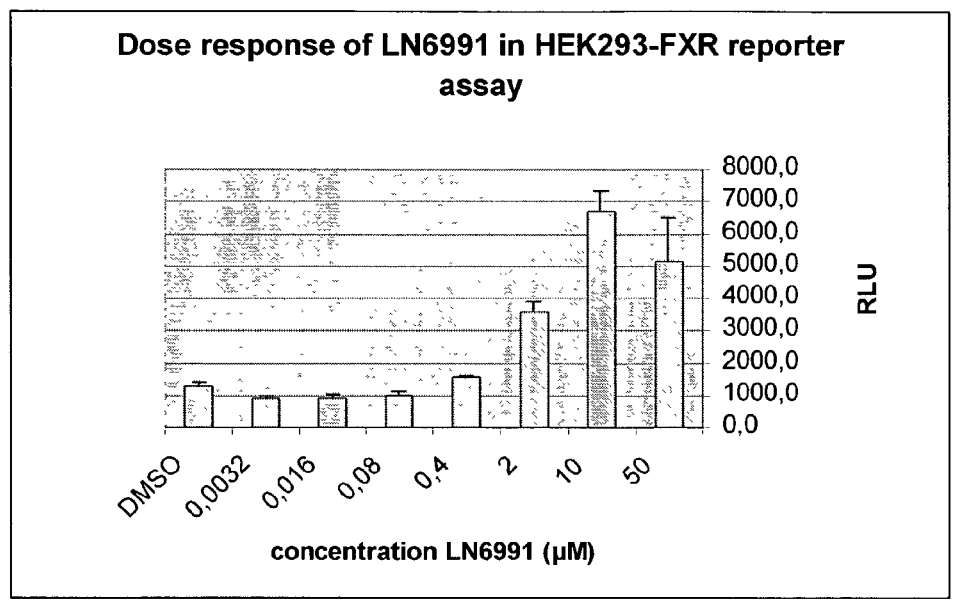
FIG. 3 shows an example for cellular reporter assay data with compound LN6691 which is an example for compounds described by formula (1).

The FXR response elements were (upper case and underlined) 5'-ccca<u>GGGTGAaTAACCT</u>cggggctctgtccctcca atccca<u>GGGTGAaTAACCT</u>cggg 3' (SEQ ID NO. 5) was created from the human IBAB-P promoter (Grober et al 1999, JBC 274, pp. 29749–29754) and integrated into the reporter plasmid pGL2promoter (Promega) according to standard methods known to those skilled in the art. A stable clone was selected and seeded at a density of 1×10$^4$ cells per well in 96 well plates. Luciferase reporter activity were determined in triplicates from extracts of cells after incubating cells in culture medium (DMEM [Gibco-BRL]+10% FCS [PAA laboratories]) for 16 hours (5% CO$_2$, 37° C.) containing 0.5% DMSO (control) or 0.5% DMSO with increasing concentrations of LN6691 (FIG. 3). The EC50 value derived in this experiment is 1.3 µM and the relative efficacy compared to the GW4064 as a control compound is about 110% (FIG. 3).

Figure 4:
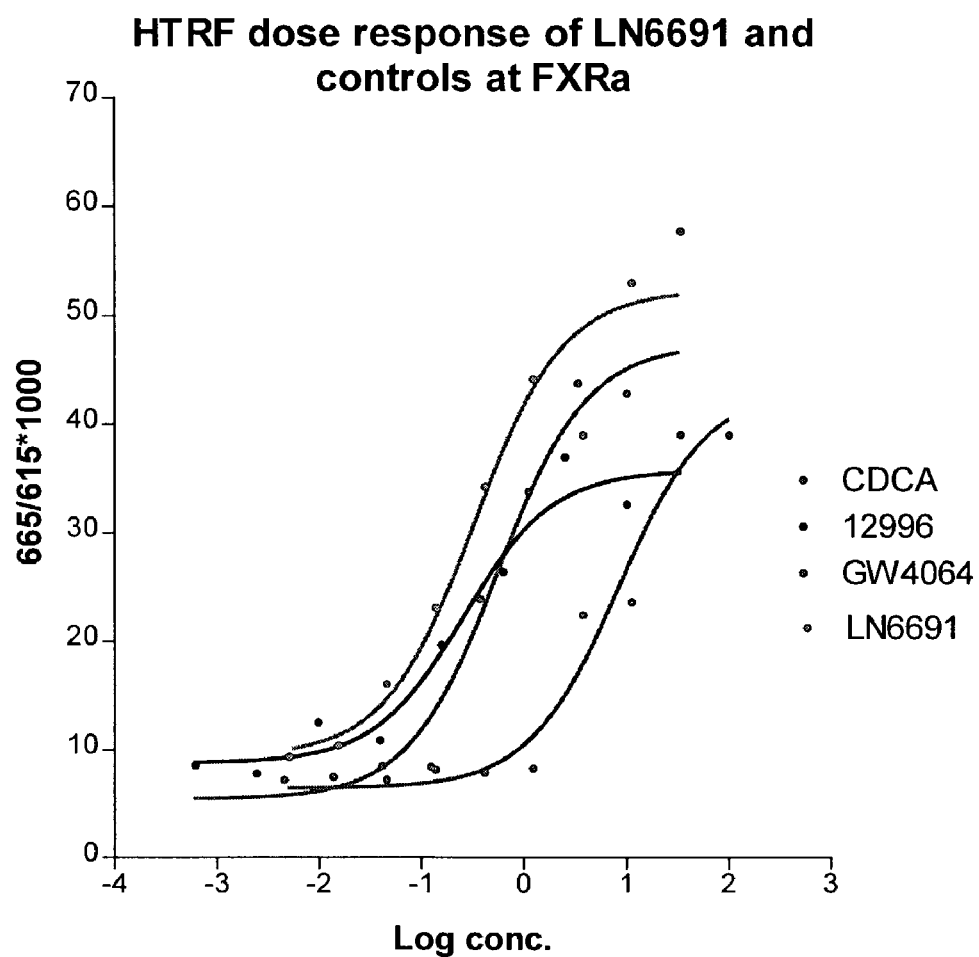
FIG. 4 shows dose response curve for LN6991, GW4064, CDCA and LN12996 as examples for dose response curves derived with the fluorescence resonance energy transfer (FRET) assay.

Preferred examples of compounds of the invention are shown below in Table 2, together with their respective EC$_{50}$ values (EC50 AVG) as established according Example 1, as well as their respective average efficacy (% activity relative to CDCA control agonist). Dose response curves done according to Example 1 for LN6991 and GW4064, CDCA and LN12996 as control compounds are shown in FIG. 4.

TABLE 2

| MOL NAME | MOLECULE STRUCTURE | EC50 AVG | EFFIC AVG |
|---|---|---|---|
| LN0000006691 | (structure) | 0.16 | 125 |
| LN0000007265 | (structure) | 0.53 | 91 |

TABLE 2-continued

| MOL NAME | MOLECULE STRUCTURE | EC50 AVG | EFFIC AVG |
|---|---|---|---|
| LN0000002683 | (structure) | 1.09 | 134 |
| LN0000006692 | (structure) | 1.66 | 111 |

While this invention has been described with reference to several preferred embodiments, it is contemplated that various alterations and modifications thereof will become apparent to those skilled in the art upon a reading of the preceding detailed description. It is therefore intended that the following appended claims be interpreted as including all such alterations and modifications as fall within the true spirit and scope of this invention.

What is claimed is:

1. A compound having the following formula (I)

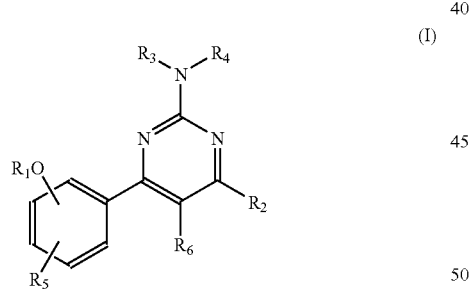

(I)

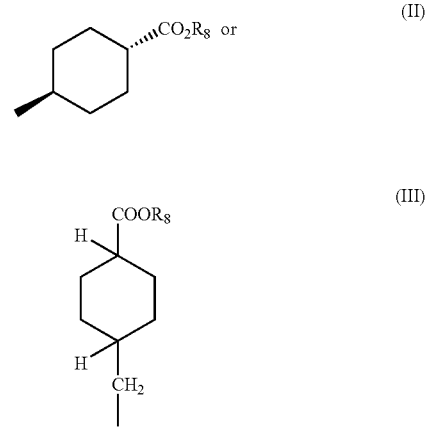

wherein:

$R_1$ in formula (I) is hydrogen, $C_1$ to $C_7$ acyl or $C_1$ to $C_7$ substituted acyl;

$R_2$ is phenyl, substituted phenyl, $C_5$ to $C_6$ heteroaryl, or $C_5$ to $C_6$ substituted heteroaryl, naphthyl, or substituted naphthyl, $R_3$ is hydrogen, $C_1$ to $C_4$ alkyl, $C_1$ to $C_{12}$ substituted alkyl, $C_7$ to $C_{12}$ alkylphenyl, $C_1$ to $C_3$ substituted alkylphenyl, and $R_4$ is a structure selected from one of the following formulas (II) or (III), or $R_3$ and $R_4$ together with the nitrogen form a heterocycle or substituted heterocycle ring;

$R_5$ is hydrogen, $C_1$ to $C_8$ alkyl, halogen, $C_1$ to $C_8$ alkoxy, carboxy, ester, amide, substituted amide or $C_1$ to $C_8$ aminoacyl;

$R_6$ is hydrogen, $C_1$ to $C_8$ alkyl, or $C_1$ to $C_8$ substituted alkyl;

$R_8$ is hydrogen, methyl or ethyl; or a resolved (diastereoisomer, enantiomer, tautomer, or a pharmaceutical acceptable salt thereof.

2. The compound of claim 1 wherein $R_1$ is hydrogen.

3. The compound of claim 1 wherein $R_2$ is selected from substituted phenyl, $C_5$ to $C_6$ heteroaryl, or $C_5$ to $C_6$ substituted heteroaryl.

4. The compound of claim 1 wherein the compound has the following formula:

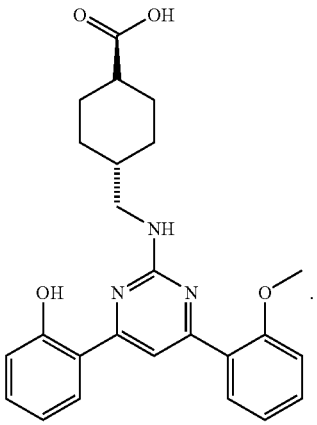

5. The compound of claim 1 wherein the compound has the following formula:

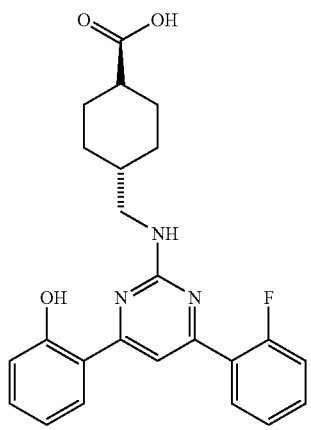

6. The compound of claim 1 wherein the compound has the following formula:

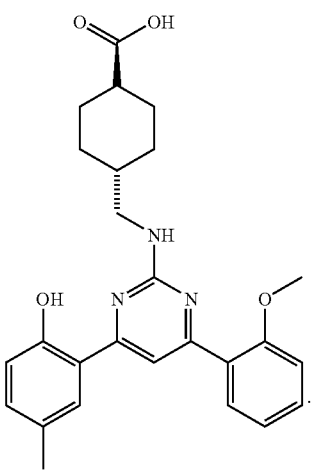

7. The compound of claim 1 wherein the compound has the following formula:

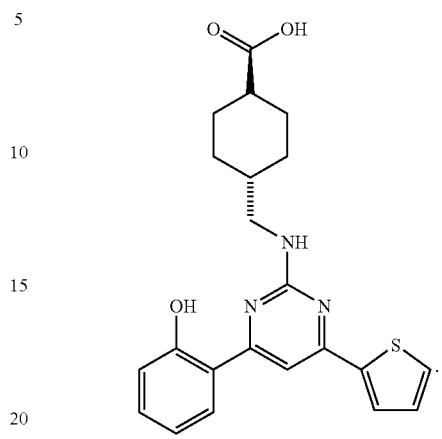

8. The compound of claim 1 or a pharmaceutically acceptable salt thereof, wherein $R_3$ is hydrogen; $R_5$ is hydrogen or a halogen; $R_6$ is hydrogen; and $R_4$ is formula (II), wherein the $COOR_8$ and the methylene substituents are in double axial (a,a) positions.

9. The compound of claim 1 or a pharmaceutically acceptable salt thereof, wherein $R_1$ is hydrogen, $R_2$ is substituted phenyl, $C_5$ to $C_6$ heteroaryl, or $C_5$ to $C_6$ substituted heteroaryl; $R_3$ is hydrogen; $R_5$ is hydrogen or a halogen; $R_6$ is hydrogen; and $R_4$ is formula (III), wherein the $COOR_8$ and the methylene substituents can adopt all possible diastereomeric configurations.

10. A method for the treatment of a disease or condition which is mediated or can be addressed by the NR1H4 receptor in a mammal comprising administration of a therapeutically effective amount of a compound according to any one of claims 1–3, 4–7, 8 and 9, wherein said disease or condition is selected from the group consisting of cholestasis and hyperlipidemias.

11. A method for regulating bile flow or the bile acid transport system in a mammal which comprises activating or repressing the NR1H4 receptor with a therapeutically effective amount of a compound according to any one of claims 1–3, 4–7, 8, and 9.

12. A method for treating in a mammal a malignant proliferative disease, which can be treated by inducing apoptosis in the affected cells or tissues comprising administering to a mammal in need of such treatment a therapeutically effective amount of a compound according to any one of claims 1–3, 4–7, 8 and 9, wherein said malignant proliferative disease is selected from the group consisting of colon cancer, ovarian cancer, metastatic heart tumors, bronchial adenocarcinoma, and lymphoma.

13. A method according to claim 10 where the mammal is a human.

* * * * *

UNITED STATES PATENT AND TRADEMARK OFFICE
CERTIFICATE OF CORRECTION

PATENT NO.       : 7,098,336 B2
APPLICATION NO.  : 10/217141
DATED            : August 29, 2006
INVENTOR(S)      : Bauer et al.

It is certified that error appears in the above-identified patent and that said Letters Patent is hereby corrected as shown below:

<u>Title Page,</u> Item (75) Inventors:

"(75)  Inventors: Ulrike Bauer, Sandhausen (DE); Zach Cheruvallath, San Diego, CA (US); Ulrich Deuschle, Bammental (DE); Elena Dneprovskaia, San Diego, CA (US); Tim Gahman, Encinitas, CA (US); Kristina Giegrich, Lampertheim (DE); Ronnie Hanecak, San Clemente, CA (US); Normand Hébert, Cardiff, CA (US); John Kiely, San Diego, CA (US); Ingo Kober, Gaiberg (DE); Manfred Kögl, Eppelheim (DE); Harald Kranz, Leimen (DE); Claus Kremoser, Heidelberg (DE); Matthew Lee, Solana Beach, CA (US); Kerstin Otte, Heidelberg (DE); Carlton Sage, Cardiff, CA (US); Manish Sud, San Diego, CA (US)"

should read

--(75)  Inventors: Ulrike Bauer, Sandhausen (DE); Zach Cheruvallath, San Diego, CA (US); Ulrich Deuschle, Bammental (DE); Elena Dneprovskaia, San Diego, CA (US); Tim Gahman, Encinitas, CA (US); Kristina Giegrich, Lampertheim (DE); Ronnie Hanecak, San Clemente, CA (US); Normand Hébert, Encinitas, CA (US); John Kiely, San Diego, CA (US); Ingo Kober, Gaiberg (DE); Manfred Kögl, Eppelheim (DE); Harald Kranz, Leimen (DE); Claus Kremoser, Heidelberg (DE); Matthew Lee, Solana Beach, CA (US); Kerstin Otte, Heidelberg (DE); Carlton Sage, Cardiff, CA (US); Manish Sud, San Diego, CA (US)--.

<u>Column 8,</u>
Line 11, "indolyi" should read --indolyl--.

UNITED STATES PATENT AND TRADEMARK OFFICE
CERTIFICATE OF CORRECTION

PATENT NO.       : 7,098,336 B2
APPLICATION NO.  : 10/217141
DATED            : August 29, 2006
INVENTOR(S)      : Bauer et al.

It is certified that error appears in the above-identified patent and that said Letters Patent is hereby corrected as shown below:

Column 8,
Line 46, "substitute alkoxy" should read --substituted alkoxy--.

Signed and Sealed this

Twentieth Day of March, 2007

JON W. DUDAS
*Director of the United States Patent and Trademark Office*